US007014823B2

(12) United States Patent
Chase et al.

(10) Patent No.: US 7,014,823 B2
(45) Date of Patent: Mar. 21, 2006

(54) BIOMOLECULAR-BASED ACTUATOR

(75) Inventors: P. Bryant Chase, Tallahassee, FL (US); Seunghun Hong, Seoul (KR); Timothy S. Moerland, Tallahassee, FL (US); Stephan Von Molnar, Tallahassee, FL (US); Peng Xiong, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 10/688,078

(22) Filed: Oct. 17, 2003

(65) Prior Publication Data
US 2004/0203071 A1    Oct. 14, 2004

Related U.S. Application Data

(60) Provisional application No. 60/419,946, filed on Oct. 18, 2002.

(51) Int. Cl.
 *B01J 8/02*   (2006.01)
 *C12M 1/00*   (2006.01)
 *C12N 9/16*   (2006.01)
 *C07K 14/00*  (2006.01)

(52) U.S. Cl. .................. 422/211; 435/283.1; 435/196; 530/350

(58) Field of Classification Search ............. 435/283.1, 435/196, 69.1; 530/350; 60/207, 721; 977/DIG. 1
See application file for complete search history.

(56) References Cited

U.S. PATENT DOCUMENTS

| 5,499,547 A | 3/1996 | Magai et al. |
| 2002/0068295 A1 | 6/2002 | Madou et al. |
| 2002/0127620 A1 * | 9/2002 | Witman et al. ............ 435/7.32 |

FOREIGN PATENT DOCUMENTS

| WO | WO 00/22101 A2 | 4/2000 |
| WO | WO 01/09181 A1 | 2/2001 |
| WO | WO 200109181 A1 * | 2/2001 |
| WO | WO 01/44302 A2 | 6/2001 |
| WO | WO 02/06789 A2 | 1/2002 |
| WO | WO 02/12896 A1 | 2/2002 |

OTHER PUBLICATIONS

Kozminski et al., "The Chlamydomonas kinesin-like protein FLA10 is involved in motility associated with the flagellar membrane," J. Cell. Biol 131(6):1517-1527, 1995.*

Thomas et al., "The physics of biological molecular motors," J Phys D: Appl Phys 31:253-266, 1998.*

Harada, et al., Mechanochemical coupling in actomyosin energy transduction studied by in vitro movement assay, J. Mol. Biol. 216:49-68 (1990).

Homsher et al., Calcium regulation of thin filament movement in an in vitro motility assay. *Biophys. J.* 70:1881-1892 (1996).

(Continued)

*Primary Examiner*—Robert A. Wax
*Assistant Examiner*—Rosanne Kosson
(74) *Attorney, Agent, or Firm*—Cooley Godward LLP

(57) ABSTRACT

This invention relates to actuators having biologically-based components, and methods of making and using the same. The actuator of the invention has a movable member that moves substantially linearly as a result of a biomolecular interaction of biologically-based components within the actuator. These actuators can be utilized in nanoscale mechanical devices to, e.g., pump fluids, open and close valves, and provide translational movement.

18 Claims, 15 Drawing Sheets

OTHER PUBLICATIONS

Huxley, Sliding filaments and molecular motile systems, J. Biol. Chem. 265:8347-8350 (1990).

Nicolau, et al. Actin motion on microlithographically functionalized myosin surfaces and tracks. Biophys. J., 77:1126-1134 (1999).

Bunk, et al., Actomyosin motility on nanostructured surfaces. *Biochem. Biophys. Res. Commun.* 301:783-788 (2003).

Chaen, et al., Lower activation energy for sliding of F-actin on a less thermostable isoform of carp myosin, *J Biochem (Tokyo)* 120:788-791. (1996).

Chase, et al. Viscosity and solute dependence of F-actin translocation by rabbit skeletal heavy meromyosin. *Am J Physiol Cell Physiol* 278:C1088-C1098 (2000).

Chomczynski et al., Single-step method of RNA isolation by acid guanidinium thiocyanate-phenol-chloroform extraction. *Anal. Biochem.* 162:156-9 (1987).

Dong, et al., Kinetic studies of calcium binding to the regulatory site of troponin C from cardiac muscle. *J. Biol. Chem.* 271:688-94 (1996).

Gordon, et al. Calcium regulation of skeletal muscle thin filament motility in vitro. *Biophys. J.* 72:1295-1307 (1997).

Hess et al., Molecular shuttles based on motor proteins: active transport in synthetic environments, *J. Biotechnol.* 82:67-85 (2001).

Hess, et al., Light-Controlled Molecular Shuttles Made from Motor Proteins Carrying Cargo on Engineered Surfaces Nano Lett. 1:235-239 (2001).

Köhler, et al., Familial hypertrophic cardiomyopathy mutations in troponin 1 (K183D, G203S, K206Q) enhance filament sliding. *Physiological Genomics* 14:117-128 (2003).

Kron, et al., Assays for actin sliding movement over myosin-coated surfaces. *Methods Enzymol.* 196:399-416 (1991).

Kunioka, et al., Innocuous labeling of the subfragment-2 region of skeletal muscle heavy meromyosin with a fluorescent polyacrylamide nanobead and visualization of individual heavy meromyosin molecules. *J Biochem (Tokyo)* 119:1024-32 (1996).

Liang, et al. Ca2+ regulation of rabbit skeletal muscle thin filament sliding: role of cross-bridge number. *Biophys. J.* 85:1775-1786 (2003).

Limberis, et al., Polarized Alignment and Surface Immobilization of Microtubules for Kinesin-Powered Nanodevices, Nano Lett. 1:277-280 (2001).

Margossian et al., Preparation of Myosin and its Subfragments from Rabbit Skeletal Muscle. *Methods Enzymol.* 85(Pt B): 55-71 (1982).

Nielsch, et al., Hexagonally ordered 100 nm period nickel nanwire arrays, Appl Phys Lett 79:1360-1362 (2001).

Potter, Preparation of troponin and its subunits, *Methods Enzymol.* 85:241-263 (1982).

Schmidt, et al., Force Tolerance of Hybrid Nanodevices, Nano Lett. 2:1229-1233 (2002).

Sellers and Kachar, Polarity and velocity of sliding filaments: control of direction by actin and of speed by myosin, Science 249:406-408 (1990).

Sidell, et al., The eurythermal myofibrillar protein complex of the mummichog (*Fundulus heteroclitus*): adaptation to a fluctuating thermal environment, J Comp Physiol 153:167-173 (1983).

Soong, et al., Powering an inorganic nanodevice with a biomolecular motor, Science 290:1555-1558 (2000).

Suzuki, et al., Control of actin moving trajectory by patterned poly(methylmethacrylate) tracks. Biophys. J. 72:1997-2001 (1997).

Toyoshima, et al., Bidirectional movement of actin filaments along tracks of myosin heads, Nature 341:154-156 (1989).

* cited by examiner

BIOMOLECULAR-BASED ACTUATOR

RELATED APPLICATIONS

This application claims priority to U.S. provisional patent application U.S. Ser. No. 60/419,946, filed Oct. 18, 2002, and hereby converts the provisional to a full utility application.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Defense Advanced Research Projects Agency (DARPA) contract N66001-02-C-8030, awarded by the Department of Defense.

FIELD OF THE INVENTION

This invention relates to actuators having biologically-based components, and methods of making and using the same. The actuator of the invention has a movable member that moves substantially linearly as a result of a biomolecular interaction of biologically-based components within the actuator. These actuators can be utilized in nanoscale mechanical devices to, e.g., pump fluids, open and close valves, and provide translational movement.

BACKGROUND OF THE INVENTION

Biological machines, and biomolecular motors in particular, have been refined through eons of evolution. Individual (or a very small number of) motors can transport cellular components within a cell, while ensembles of very large numbers of motors are arranged to move the largest creatures on earth. Nanoscale engineering by humans can be greatly enhanced by assimilation of biological specialization already achieved through natural evolution, and by envisioning additional modifications through molecular genetics.

Increasing demand for in situ characterization and quantification of samples in complex systems has stimulated the development of miniaturized chemical analysis systems that automatically perform multiple steps such as sampling, transport, separation, and detection. See Hess, et al., J. Biotechnol. 82:67–85 (2001); Schmidt, et al., Nano Lett. 2:1229–1233 (2002); and Soong, et al., Science 290:1555–1558 (2000). Crucial to these systems is the availability of nano-mechanical devices, i.e., nanoscale motors, that provide the necessary locomotive forces. Because production of nanoscale motors has proven challenging, a recent focus has been on adapting the highly efficient, naturally occurring nanoscale motor proteins kinesin and myosin, coupled with microtubules and actin filaments, respectively. In vitro interactions between actin and myosin, two major muscle proteins, powered by the hydrolysis of adenosine triphosphate (ATP), can produce movement and force in the same way they drive muscle contractions. The success of a device comprising the actomyosin system depends on the proper interfacing/immobilization of the proteins to synthetic nanomechanical components. Surfaces used should be biocompatible and patterned in a way that would allow ordered and controllable actomyosin, kinesin/microtubule interactions. Nanostructured surfaces having submicrometer grooves have been produced, using electron beam lithography and UV photolithography, to restrict actomyosin motility to specified areas. Nicolau, et al. Biophys. J., 77:1126–1134 (1999); Suzuki, et al., Biophys. J. 72:1997–2001 (1997); and Bunk, et al., Biochem. Biophys. Res. Commun. 301:783–788 (2003). Sufficiently narrow grooves constrain filament motion to a track and minimize the number of filaments that change direction. Motor proteins, however, were located both within and between tracks, rendering the complete restriction of the actomyosin interaction to the patterned areas somewhat difficult to achieve. We have now discovered certain improvements in the art of nanoscale motors and devices.

SUMMARY OF THE INVENTION

One aspect of the invention provides an actuator having a movable member that moves substantially linearly as a result of a biomolecular interaction of biologically-based components within the actuator. Preferably, the movable member is coated at least in part with a first interactive biological material. In a preferred embodiment, the biologically-based components comprise a first interactive biological material and a second interactive biological material. The interactive biological materials may be protein, preferably myosin and actin, respectively. Movement of the movable member may by unidirectional or bidirectional. The invention also includes combinations of at least two actuators wherein the actuators function in concert.

In another aspect, the invention provides an actuator having a movable member that moves substantially linearly as a result of a biomolecular interaction of myosin and actin within the actuator, wherein two separate, parallel arrays of actin filaments are aligned along the same axis of a stationary member but with opposite polarities and both arrays are positioned to interact with myosin that is coated on the movable member; and a separate energy-transmitting stripe is associated with each actin array in a manner to selectively energize an actin array so that when one of the stripes is sufficiently energized, the actin/myosin interaction is such that the moveable member is moved from its starting position in a direction parallel to the actin filaments within the array. Preferably, the movable member is a rod, the actin filaments within the parallel actin arrays are parallel to the rod's longitudinal axis, and the rod is moved in a direction of its longitudinal axis.

The invention also provides, an actuator having a movable member that moves substantially linearly as a result of a biomolecular interaction of a first interactive biological material with a second interactive biological material within the actuator wherein the second interactive biological material is inert unless associated with a source of energy. The energy converts the second interactive biological material into a modified energy state so that it interacts with the first biological material to cause the movable member to move relative to a starting position.

Yet another aspect of the invention provides an actuator having a movable member having a biocompatible molecular layer deposited on the surface thereof and a layer of myosin, or fragment thereof, adhering to at least a portion of the biocompatible molecular layer that moves substantially linearly as a result of a biomolecular interaction of the myosin coating with at least one array of actin filaments attached to a stationary. The actuator further comprises an energy-transmitting stripe associated with the actin array in a manner to energize the actin array, wherein the actin array is inert unless energized; a well containing a substance that is a source of chemical potential energy that aids the interaction of myosin with actin, the well being positioned to retain the substance in contact with the actin array and the myosin layer; and a hydrophobic region positioned on opposite sides of the well to slidingly engage the rod and retain the substance within the well, wherein when the energy-transmitting stripe is sufficiently energized, the actin/myosin interaction is such that the movable member is moved in a direction parallel to the actin filaments within the array.

In another aspect, the invention provides a fluid delivery device that comprises an actuator having a movable member that moves substantially linearly in a direction as a result of biomolecular interaction of biologically-based components within the actuator; a reservoir for containing a fluid, an exit orifice from the reservoir, wherein the actuator is positioned between the reservoir and the exit orifice such that the movable member in a closed position blocks the flow of fluid from the reservoir to the exit orifice but allows fluid to flow when the biomolecular interaction of the biologically-based components within the actuator cause the member to move to an open position.

Another aspect of the invention provides a rod having a biocompatible molecular layer or layers deposited on the surface of the rod and a layer of a protein or fragment thereof that aids in the contraction or relaxation of muscle adhering to at least a portion of the biocompatible molecular layer(s). Preferably, the rod's longitudinal dimension is about 100 nanometers (nm) to about 100 microns and the rod's cross sectional dimension is about 5 nm to about 200 nm. One anticipated use of the invention includes delivering the rod of the invention to the interior of the cell where the myosin coating of the rod will interact with the naturally occurring actin filaments of the cell.

Yet another aspect of the invention provides a process for making an actuator having a biocompatible molecular layer deposited on the surface of the rod and a layer of a protein or fragment thereof that aids in the contraction or relaxation of muscle adhering to at least a portion of the biocompatible molecular layer, which method comprises depositing a biocompatible molecular layer on the surface of a rod and adhering a layer the protein, or fragment thereof, onto the biocompatible molecular layer. Preferred methods of depositing the biocompatible molecular layer include stamping techniques and dip-pen nanolithography techniques.

The invention also provides well structure for use in the biomolecular-based actuator, which structure comprises at least one array of protein filaments positioned to interact with a protein coat on a movable member having a biocompatible molecular layer deposited on the surface of the member, where the protein coat adheres to at least a portion of the biocompatible molecular layer; an energy-transmitting stripe associated with the array in a manner to selectively energize the array; a well containing a substance of chemical potential energy that aids the interaction of the protein coat on the movable member with the array, the well being positioned to retain the substance in contact with the array and the protein coat; and a hydrophobic region positioned on opposite sides of the well to slidingly engage the movable member and retain the substance within the well. Preferably, the movable member is a rod; the array is an array of actin filaments; the protein coat comprises myosin, myosin S1, or heavy meromyosin; two separate parallel arrays of actin filaments are aligned along the same axis but with opposite polarities, each array of actin filaments being aligned parallel to the longitudinal axis of the rod and positioned to interact with the myosin coating; and a separate energy-transmitting stripe associated with each array of actin filaments in a manner to selectively energize an actin filament array so that when one of the energy-transmitting stripes is sufficiently energized, the actin/myosin interaction is such that the rod is moved along its longitudinal axis from its starting position in a direction parallel to the filaments within the actin array.

Another aspect of the invention provides a process for making the well structure described above. The method of the invention comprises providing a reservoir having an inside surface and two orifices positioned opposite each other and suitable for receiving a movable member through each orifice; positioning at least one array of a protein on the inside surface of the reservoir; positioning an energy-transmitting stripe in contact with the array so that the end of the stripe away from the protein array may be connected to an energy source; and providing a hydrophobic region at each orifice to slidingly engage a movable member through each orifice and provide a seal for aqueous liquid when placed in the reservoir. In a preferred embodiment, two separate, parallel arrays of actin filaments are aligned along the same axis but with opposite polarities and are positioned on the inside surface of the reservoir but spaced from each other, and a separate energy-transmitting stripe contacts each array in a way to selectively energize an actin filament array.

One aspect of the invention provides a process for preparing an actuator comprising providing a movable member; depositing a first protein that aids in the contraction or relaxation of muscle on at least a portion of the surface of the movable member; providing a reservoir having (a) an inner surface having an array of a second protein that interacts with the first protein deposited on the inner surface, (b) an energy-transmitting strip contacting the second protein so that the end of the stripe away from the array can be connected to an energy source, and (c) two orifices opposite each other to receive the movable member so that the first protein can be positioned within the reservoir; and providing a substance that is a source of potential chemical energy to aid in the interaction of the first and second proteins, wherein, when energy is transmitted to the second protein the movable member moves from a starting position to a different position.

Yet another aspect of the invention provides a combination of a Hall gradiometer with an actuator having a movable member that moves as a result of biomolecular interaction of a biologically-based components within the actuator, wherein the movable member has a magnetic field associated with it so that the motion of the movable member is detected by measuring the fringe magnetic field of the movable member in the gradiometer. The combination optimally operates at a temperature of about 0° C. to about 70° C. One preferred embodiment incorporates a feedback mechanism between the gradiometer and the actuator. The feed back signal can be used to improve accuracy and speed of actuator motion.

BRIEF DESCRIPTION OF THE DRAWINGS

In FIG. 3A, the first pattern is generated via MHA molecules with alignment marks. In FIG. 3B, the coordinates of the second pattern are calculated in the computer based on the AFM image of alignment marks on the surface. The calculated coordinates are utilized to generate the second molecular patterns with ODT molecules. FIG. 3C illustrates the final results.

FIG. 12B shows a snapshot of fluorescently labeled actin filaments sliding in channels (PAH) of 3.98 μm width. The dotted arrows show the trajectories followed by two filaments.

FIG. 13A illustrates a nano-rod coated with myosin. FIG. 13B shows the ATP well with two heater stripes and polar actin filament arrays. FIG. 13C depicts an assembled nano-actuator. Hydrophobic sealing prevents leakage of the ATP solution. FIG. 13D illustrates reversible linear actuation controlled via temperature.

DETAILED DESCRIPTION OF THE INVENTION

Figure 1:
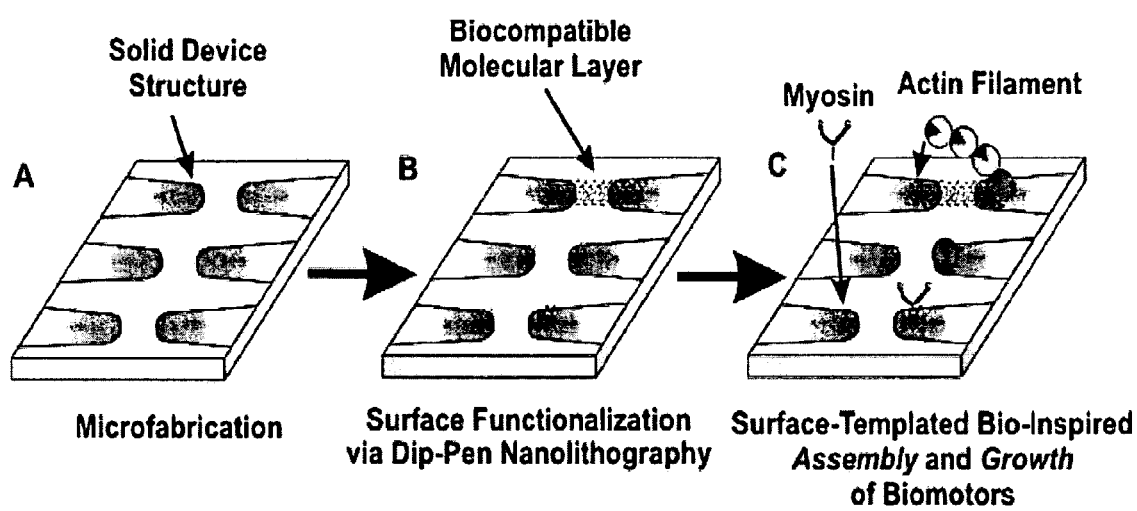
FIG. 1 provides a schematic diagram depicting three basic steps for nano-assembly process of biomotor devices.

An "actuator" is a mechanical device for moving or controlling something.

The terms "substantially linearly" and "substantially linear movement" refer to the phenomenon by which two surfaces having associated biological components interact and shift past one another in a predominantly linear direction, e.g., relative to the longitudinal axis of the moving member. If one of the surfaces is curved, the movement is linear relative to the two surfaces at their point of interaction. However, the curved member will, as a whole, move along the arc of the curve.

The term "rod" refers to a physical object wherein one dimension of the object (e.g., the length) exceeds its cross-sectional dimensions (e.g., the height and width). The long dimension of the object is referred to as the "longitudinal axis." The cross-section of the longitudinal axis is polygonal, elliptical, circular, etc., but preferably is circular. The cross section of the rod may vary along the longitudinal axis, but preferably is uniform. The longitudinal axis may be straight or curved, but is preferably straight.

"Biocompatible" as used herein means a material characteristic that allows interaction with a biological entity without producing a toxic or injurious response.

The term "chemical potential energy" refers to energy that is stored within a bond or bonds of a chemical entity. The energy is released by cleavage of the bond(s) storing the chemical potential energy.

"Myosin" refers to any member of a family of motor ATPases that interact with actin filaments. An increasing number of different myosins are being described. For example, Brush border Myosin I is a single headed myosin found in the microvilli of vertebrate intestinal epithelial cells, linking the membrane to the microfilament core. Myosin II is the classical sarcomeric myosin that self assembles into bipolar thick filaments. Between species and tissues there are considerable variations in the properties of Myosin II. Cytoplasmic myosin II is a family of sarcomeric myosin like proteins responsible for force generation by interaction with microfilaments. Myosins III, IV, V and VI have also been identified and would fall within the scope of the term "myosin."

"Meromyosin" refers to fragments of myosin formed by proteolytic, e.g., trypsin or chymotrypsin, digestion. Heavy meromyosin (HMM) has the hinge region and ATPase activity. Light meromyosin (LMM) is mostly helical and is the portion normally laterally associated with other LMM to form the thick filament itself.

Actuators of the Invention

The actuator of the invention comprises a movable member that moves substantially linearly as a result of biomolecular interaction of biologically-based component within the actuator. The general purpose components and methods of the invention will permit the construction of a wide variety of devices. Examples of devices that might incorporate the actuators of the invention include valves in microfluidics, gates for controlled release of substances (e.g., neutralizing agents), movement of a shutter for control of optical pathways, or synthetic chromatophore (artificial camouflage). The actuator will generally be less than 100 microns in length in any of its 3 dimensional measurements.

In addition to the movable member, an actuator of the invention preferably comprises two separate, parallel arrays of actin filaments aligned along the same axis of the a stationary member but with opposite polarities and both arrays are positioned to interact with myosin that is coated on the movable member and a separate energy-transmitting stripe associated with each actin array in a manner to selectively energize an actin array so that when one of the stripes is sufficiently energized, the actin/myosin interaction is such that the movable member is moved from its starting position in a direction parallel to the actin filaments of the activated array. In a preferred embodiment, the movable member is a rod and the actin filaments within the parallel actin arrays are parallel to the rod's longitudinal axis, such that the rod is moved in the direction of its longitudinal axis.

In another embodiment of the invention, the actuator further comprises a movable member having a biocompatible molecular layer deposited on the surface thereof and a layer of myosin, or fragment thereof, adhering to the rod and optionally to at least a portion of the biocompatible molecular layer; at least one array of actin filaments positioned to interact with the myosin coating; an energy-transmitting stripe associated with the actin array in a manner to energize the actin array; a well containing a substance that is a source of chemical potential energy that aids the interaction of myosin with actin, the well (a) being positioned to retain the substance in contact with the actin array and the myosin layer and (b) having opposite orifices to slidingly engage the movable member; and a hydrophobic region positioned on opposite sides of the well to retain the substance within the well when the movable member is slidingly engaged. When the energy-transmitting stripe is sufficiently energized (e.g. heated), the actin/myosin interaction is such that the movable member is moved in a direction parallel to the actin filament.

Another aspect of this invention is a fluid delivery device that comprises a reservoir for containing a fluid, an exit orifice from the reservoir, and the actuator characterized as in the previous discussion. The actuator is positioned between the reservoir and the exit orifice such that the movable member in a closed position blocks the flow of fluid from the reservoir to the exit orifice but allows fluid to flow when the biomolecular interaction of the biologically-based components within the actuator cause the member to move to an open position.

The invention also provides a process for preparing an actuator of this invention, which comprises:

providing a movable member;

depositing a first protein that aids in the contraction or relaxation of muscle on at least a portion of the surface of the movable member;

providing a reservoir having (a) an inner surface having an array of a second protein that interacts with the first protein deposited on the inner surface, (b) an energy-transmitting stripe contacting the second protein so that the end of the stripe away from the array can be connected to an energy source, and (c) two orifices opposite each other to receive the movable member so that the first protein can be positioned within the reservoir; and providing a substance that is a source of potential chemical energy to aid in the interaction of the first and second proteins, wherein, when energy is transmitted to the second protein the movable member moves from a starting position to a different position.

Preferably, a hydrophobic region, particularly a hydrophobic collar, is positioned at each orifice to aid in retaining the source of potential chemical energy, e.g., ATP or 2'-dATP, within the reservoir. Each of the components of the actuator of the invention is discussed in greater detail below.

Yet another aspect of the invention is a combination of a Hall gradiometer with an actuator having a movable member that moves as a result of biomolecular interaction of a biologically-based components within the actuator, wherein the movable member has a magnetic field associated with it so that the motion of the movable member is detected by measuring the fringe magnetic field of the movable member in the gradiometer Movable Member One aspect of this invention is an actuator having a movable member that moves as a result of biomolecular interaction of biologically-based components within the actuator, i.e., a biomolecular motor drives the actuator. Preferably, the movable member is in the shape of a rod and is coated at least in part with a first interactive biological material.

Another aspect of the invention is a movable member, particularly a rod, having a biocompatible molecular layer deposited on the surface of the rod and a layer of a protein (or fragment thereof) that aids in the contraction or relaxation of muscle adhering to at least a portion of the biocompatible molecular layer. Proteins that aid in the contraction or relaxation of muscle include, inter alia, myosin or the calcium responsive proteins, troponin or tropomyosin.

The movable member useful in the actuator of this invention will have several characteristics that allow it to operate as desired. The member will be a solid material that will preferably have a surface that is amenable to deposition of a biocompatible molecular layer and/or the interactive biological material such as a protein on its surface. The solid material will be firm in nature and will have a defined shape and volume, i.e., it is not a liquid or gas. The shape of the solid member will be a shape that allows the member to move within the actuator. Thus, the member may be viewed as a sheet (i.e., a broad, thin preferably rectangular material), a rod, or the like. If a rod, it is preferably cylindrical with an approximately circular (or oval) cross-section perpendicular to the longitudinal axis, but may have a cross-section that is polygonal, i.e., triangular, square, rectangular, hexagonal, etc.

The movable member may be any dimension that permits it to function within the actuator. Preferably, the movable member is a rod with a longitudinal axis about 100 nm to about 100 $\mu$m in length and a cross-section of about 20 nm to about 200 nm.

The movable member is composed of a material that may be organic (i.e., carbon-based), or inorganic, but will preferably have a surface upon which a biocompatible molecular layer can be deposited. Thus, the material may be polymeric, a pure metal, a mixture of metals (e.g., an alloy or an amalgam), or a solid with a pure metal, a mixture of metals, silicon dioxide or other material deposited thereon. Preferably, the solid movable member is a material (e.g., a metal) that exhibits a dipole field that can be measured when the material moves. Thus, it may be, e.g., a polymer having particles of magnetic iron arranged to provide a dipole. Preferred materials include nickel, palladium, gold, platinum, cobalt, permalloy, chromium, or mixtures thereof.

Over the years a host of methods have been developed for the fabrication of metal rods with diameters varying between a nanometer to hundreds of nanometers. Exemplary methods for producing the movable members of the invention include, but are not limited to, electron beam lithography and electro-chemical deposition which can be used to synthesize metal nanorods over a wide range of diameters and lengths.

One aspect of the invention provides a process for making the rod described above, which method comprises depositing a biocompatible molecular layer on the surface of a rod and adhering a layer the protein, or fragment thereof, onto the biocompatible molecular layer. The rod may be prepared by any one of a variety of methods known in the art. For example, the rods may be made by electron beam lithography or electrochemical deposition.

Electron beam lithography involves electron beam definition of a resist layer, deposition of the metal film, and solvent liftoff. Usually a bilayer polymethylmethacrylate/methylmethacrylate (PMMA/MMA) resist is used so that the resist pattern after development has a bilayer structure with an overhang to facilitate easy liftoff. Thin film deposition tools include thermal and electron-beam evaporation, sputtering, pulsed laser ablation, and molecular beam epitaxy. In particular, to make rods composed of nickel, magnetron sputtering and ultrahigh vacuum electron beam deposition are preferred methods. After the deposition of the metal film, the entire sample is immersed in solvent to wash away the residual resist and metal, leaving only the nanorods on the substrate. The nanorods can be retrieved by etching the substrate with a selective etchant (KOH, e.g.) which does not attack the metal. The free nanorods can then be collected via centrifugation. Magnetic rods can also be collected using a magnet. This method is flexible and has fast turn-around time. Nickel nanorods were fabricated this way for the recent demonstration of coupling to the rotational motion of biomotors. Soong, et al., Science 290:1555–1558 (2000).

For large-scale production of nanorods, electrochemical deposition through anodic alumina containing a regular array of nanopores is a preferred production method. These nanopores are obtained by electrochemical anodization of aluminum metal, and the pore diameter and length can be readily controlled and varied over a large range. Alternatively, polycarbonate templates may be used for electrochemical deposition. The anodic alumina nanopore template has been used to grow a wide variety of metal and semiconductor wires by several different methods. A recent refinement of the technique via a two-step process has resulted in well-ordered nanopores with sharply-defined pore diameters. Masuda and Fukuda, Science 268:1466 (1995) and Nielsch, et al., Appl Phys Lett 79:1360 (2001). Now these nanopore templates are available commercially, e.g., from Whatman International LTD., with diameters ranging from 30 nm to millimeters and length to hundreds of millimeters. A metal, Au, e.g., layer can be deposited on one side as the base electrode for electro-deposition. A second metal (Ni, e.g.) can then be deposited and fill the nanopores. The length of the wires can be precisely controlled by counting the total charge. An important advantage of this technique is that the nanorods can be grown in such a way so that they contain sections of different materials, offering much needed flexibility in subsequent functionalization. For example, Ni wires with gold tips at the two ends can be grown. Once the growth is finished, the alumina matrix can be dissolved with an appropriate base and the wires can be collected by centrifugation or magnet. In the case of polycarbonate templates, the template can be dissolved with $CH_2Cl_2$.

In another embodiment of the invention, the movable member comprises a polymeric material. For example, a rod of the invention can be a carbon nanotube, optionally filled with a magnetic material.

Biocompatible Molecular Layers

One of the most challenging problems in biomotor device applications is the development of reliable nano-assembly processes. To build any practical mechanical devices with protein motors, one needs to be able to assemble motor components on solid substrates with a desired position and polarities. Conventional microfabrication processes usually involve polymer resist layers and temperature heating up to 100° C. while most motor proteins are chemically reactive and become inactive at temperatures greater than 60° C. Thus, conventional microfabrication methods generally are not compatible with protein motor components.

The biocompatible molecular layer may be deposited on the movable member by any one of a variety of techniques. In one preferred embodiment, the biocompatible molecular layer is deposited on the rod using a dip-pen nanolithography (DPN) technique to result in a biocompatible molecular layer that is about 1 nm to about 200 nm in thickness. The biocompatible molecular layer circumscribes at least a portion of the length of the movable member. Preferably the biocompatible molecular layer is a self-assembling monolayer. The biocompatible molecular layer is selected to promote attachment of a biological component, e.g., a protein. Preferably the protein is myosin.

Attachment of the biological components to the stationary and movable members of the actuators of the invention involves three conceptual steps as indicated in FIG. 1. The first step involves photolithographic deposition of patterned electrodes on solid substrates. The second step involves using biocompatible nanoscale patterning deposition to template functional groups, such as the biocompatible molecular layer, onto the substrates. Finally, in the third step protein motors and other components are assembled at the desired locations via direct binding to functionalized domains, i.e., the biocompatible molecular layer. Any complicated biomotor structures can be assembled simply repeating these basic steps.

Figure 2:
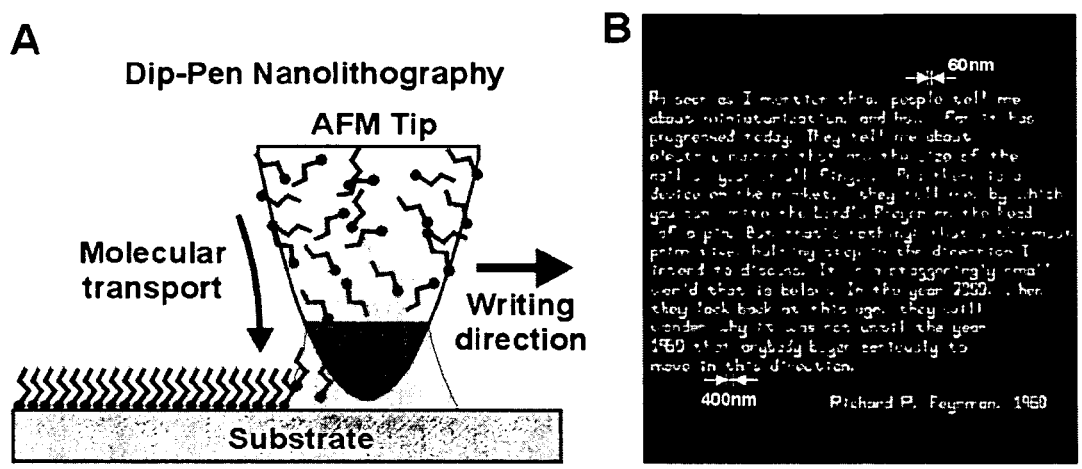
FIG. 2A is a schematic diagram depicting dip-pen nanolithography process (DPN).
FIG. 2B demonstrates nanoscale molecular patterns written with 16-mercaptohexadecanoic acid via dip-pen nanolithography.
Figure 3:
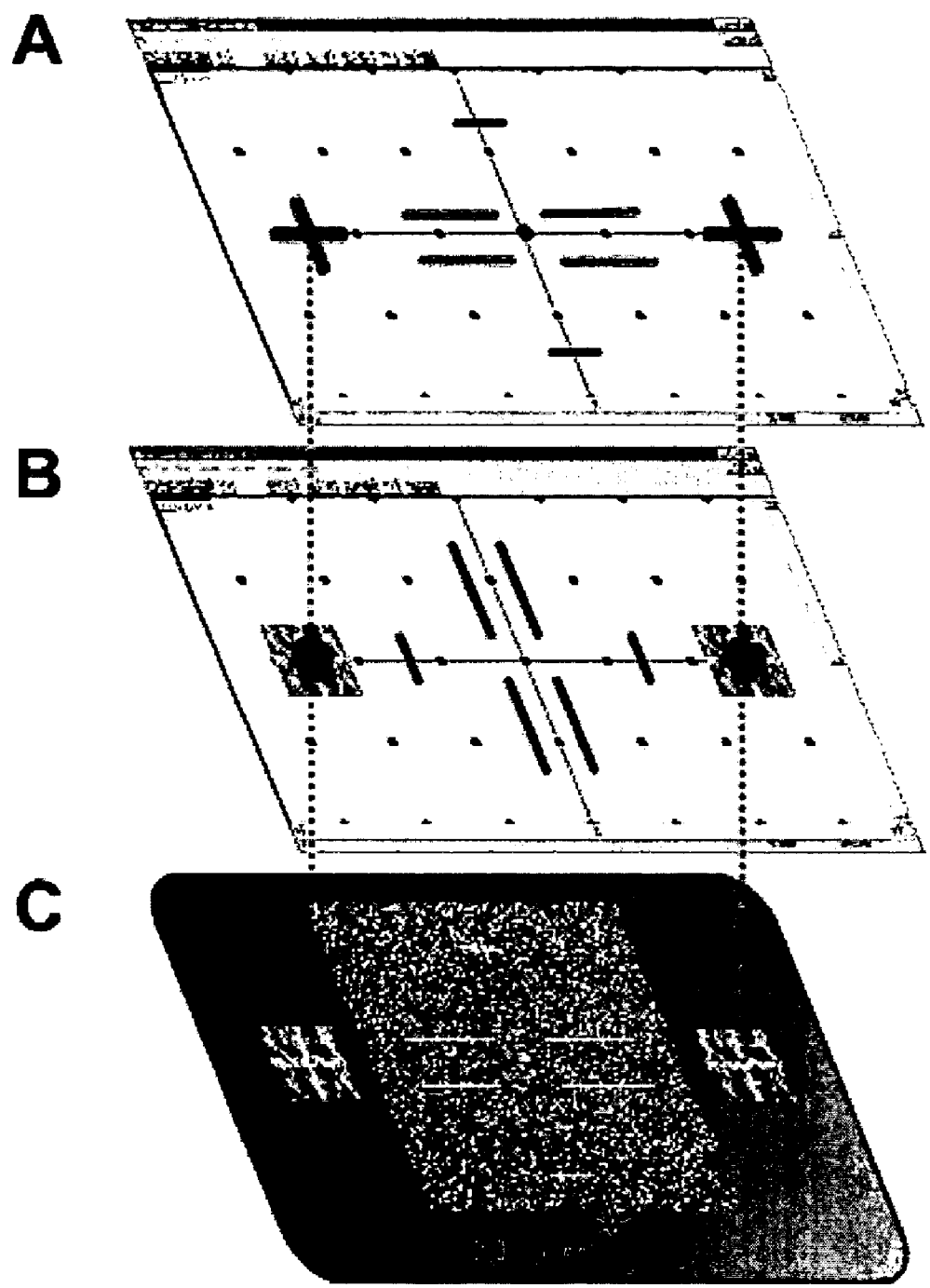
FIG. 3 depicts a method to generate multiple soft nanostructures utilizing DPN software.

Recent development of dip-pen nanolithography provides an ideal tool for rapid fabrication of molecule-based structures. The DPN process is a direct deposition technique that utilizes an atomic force microscope (AFM) tip as a pen, molecular substances as ink, and solid substrates as paper (FIG. 2A). As the AFM tip is translated relative to the sample, the deposited ink forms a patterned, biocompatible molecular layer on the substrate. A number of variables, including relative humidity, temperature, and tip speed, can be adjusted to control ink transport rate, feature size, and linewidth. The DPN technique permits lithography of unprecedented resolution. Considering that conventional direct deposition technology such as an ink jet printer has a minimum feature size of ~10 $\mu$m, current resolution of DPN (~5 nm) means a revolution in direct printing technology. Direct self-assembled monolayer (SAM) patterning on this scale has never been demonstrated by any other techniques. Combined with new design software, DPN allows one to directly print out designed patterns onto the substrate, which minimizes the processing time and increase the speed of a research cycle (FIG. 2B). Because DPN allows one to image nanostructures with the same tool used to form them, one can use DPN to generate and align nanostructures with pre-existing patterns on the substrate with ultrahigh registration (FIG. 3).

The functionalized substrates may be used to assemble heavy meromyosin (HMM) or myosin onto specific substrate areas. Since these motor proteins contain long alpha-helical coiled-coil "tails" at the end of them, they may not be suitable for direct deposition via DPN. This is an even greater problem fro actin filament, which are longer than myosin molecules. In the assembly process, solid substrates are functionalized with molecular layers (linker molecules) with strong affinity to myosin and they are placed in a myosin solution to capture the motor proteins. Various linker molecules have been utilized to enhance the assembly of HMM on solid substrates. These include hexamethyldisilazane (HMDS), fluoropolymers, poly(methylmethacrylate) (PMMA), and nitrocellulose.

In another preferred aspect, the actuator employs a movable member having a gold surface coated with a biocompatible molecular layer that comprises a protein or peptide or a compound with the formula $R^1SH$, $R^1SSR^2$, $R^1SR^2$, $R^1SO_2H$, $(R^1)_3P$, $R^1NC$, $R^1CN,(R^1)_3N$, $R^1COOH$, or ArSH, wherein:

$R^1$ and $R^2$ each has the formula $X(CH_2)_n$ and, if a compound is substituted with both $R^1$ and $R^2$, then $R^1$ and $R^2$ can be the same or different;

n is 0–30;

Ar is an aryl;

X is —$CH_3$, —$CHCH_3$, —COOH, —$CO_2(CH_2)_m$—OH, $CH_2OH$, ethylene glycol, hexa (ethylene glycol), $O(CH_2)_mCH_3$, —$NH_2$, —$NH(CH_2)_mNH_2$, halogen, glucose, maltose, fullerene C60, a nucleic acid, a protein, or a ligand; and m is 0–30.

Specifically, the biocompatible molecular layer may be a compound such as propanedithiol, hexanedithiol, octanedithiol, n-hexadecanethiol, n-docosanethiol, 11-mercapto-1-undecanol, α,α-p-xylyldithiol, 4,4'-biphenyldithiol, terphenyldithiol, or DNA-alkanethiol.

Where the movable member has a surface of silicon dioxide, the biocompatible molecular layer compound is a protein or peptide or has the formula $R^1SH$ or $R^1SiCl_3$, wherein $R^1$ has the formula $X(CH_2)_n$;

n is 0–30.

X is —$CH_3$, —$CHCH_3$, —COOH, —$CO_2(CH_2)_mCH_3$, —OH, —$CH_2OH$, ethylene glycol, hexa(ethylene glycol), —$O(CH_2)_mCH_3$, —$NH_2$, —$NH(CH_2)_mNH_2$, halogen, glucose, maltose, fullerene C60, a nucleic acid, a protein, or a ligand; and m is 0–30.

Particularly useful compounds are octadecyltrichlorosilane or 3-(2-aminoethylamino)propyltrimethoxysilane.

Thiol-functionalized S1 units may be directly deposited on an Au surface via dip-pen nanolithography (DPN) to form a nanometer-scale motor array. Myosin S1 is sufficient to move actin filament in vitro, with a motility similar that of heavy meromyosin (HMM). The motor function of S1 on the gold surface is confirmed by observing sliding movement. 30 nm linewidth protein lines can be directly generated via DPN without any complicated process.

In another preferred embodiment, proteins can be assembled on a Ni substrate via commercially available biotin-His tag peptides and streptavidin. Layers involving streptavidin and biotinylated molecules work well for the Ni nanorods. Biotinylated HMM can be attached to Ni rods using (1) a commercially available, biotinylated His-tag peptide that binds to Ni rods, (2) commercially available, biotinylated streptavidin that binds to the biotinylated His-tag peptide, and finally (3) biotinylated HMM that has biotin covalently bound to the "tail" portion of HMM, i.e., distal from the motor domain. Biotinylated AMM can be prepared according to the protocol of Kunioka, and Ando, *J Biochem* (*Tokyo*) 119:1024–32 (1996).

The actin-attached surface may be prepared by a variety of techniques. For example, gelsolin can be directly deposited on substrates. The first step for this process is direct or indirect deposition of the protein gelsolin on specific positions. Native gelsolin has $Ca^{2+}$ dependent activity of severing an actin filament, capping the barbed end of the actin filament, and forming a polymerization nucleus as the complex with two actin monomers. The gelsolin can be directly deposited on the substrates via DPN or indirectly assembled onto molecular layers with active terminal groups such as carboxylic acid or amine. Patterned gelsolin on the surface can be utilized as a nucleation site for actin filaments. Alternatively, the gelsolin site can be utilized to capture the barbed end of actin filaments. The fully-grown actin filaments will be trapped on the molecular layers.

In the second step, DPN will be utilized to draw linear organic patterns from the gelsolin site. These lines define the directions of actin filaments. Similar linker molecules as those used for myosin are also known to have a strong affinity to the actin filaments and will be utilized for assembly of actin filaments.

A simple alternate approach to the fabrication of patterned microstructures is the use of wet microcontact printing techniques. Here, we describe a novel approach to prepare actomyosin compatible surfaces, using polyelectrolyte multilayers (PEMUs). This microprinting, or "stamping", technique can be used for patterning may of the compounds described above for DPN. In this technique, a layer of Au is made, the stamp is coated with the desired compound and then deposited on the Au surface. The remaining Au regions between patterns are then coated with a second, "passivating" or other, compound, i.e., a compound with a functional group different than the first "desired" compound, by flooding the area with the second compound. These surfaces are rugged, amorphous nanocomposites prepared by the layer-by-layer assembly method. They offer a wide range of compositional flexibility, permitting optimization of the surface-nanomotor interaction and are compatible with wet contact printing methods. A positively charged terminal layer allowed rabbit skeletal muscle HMM to bind and retain motor function. Microstructured channels for motility were created on these PEMUs by using polydimethyl siloxane (PDMS) stamps and PEBSS [Poly(styrene sulfonate)-block-poly(ethylene-ran-butylene)-block-poly(styrene sulfonate)] a negatively charged hydrophobic polymer as the inking solution to produce barriers.

Alternatively, the surface can be prepared using poly (dimethylsiloxane) elastomeric stamps. Microcontact printing may be used to create polymer patterned surfaces on multilayers (polymer-on-polymer stamping, or POPS). In POPS the surface of a stamp is inked with polymer and, after drying, the stamp is pressed on the top of a multilayer. A polyelectrolyte of opposite charge to the surface facilitates adhesion. PEBSS may be used to create water insoluble walls to delineate channels with PAH on the bottom of the channel. The hydrophobic nature of the inking solution eliminates the need to oxidize the PDMS surface with $O^2$ plasma to make it more wettable.

Figure 4:
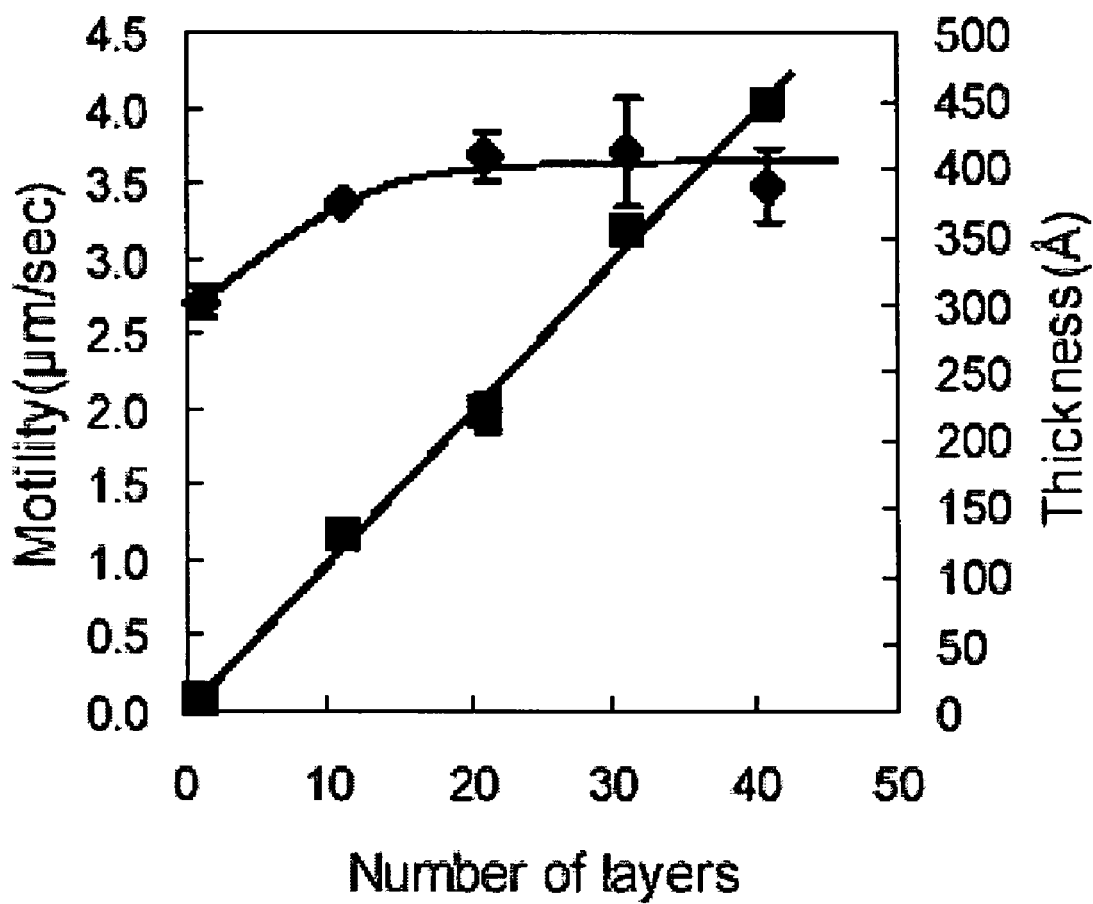
FIG. 4 illustrates the speed and thickness versus number of polyelectrolyte layers. Diamonds represent average speed of actin filaments on multilayer surfaces with different thicknesses. Squares show the increase in film thickness as more layers are adsorbed. Thickness was determined using ellipsometer.

The use of a polyelectrolyte multilayer permits a multi-composite, multifunction approach to integrating bionanomotors into a functional package. PEMUs may be designed with layers of active materials, such as enzymes, embedded in them and may have functions other than promoting protein adhesion, such as controlling permeability, electrical conductivity, sensors, nanoporosity and swelling. The average speed of actin filaments was determined on the myosin functionalized PAH monolayer/multilayer by computer analysis of digitized movies. Filament sliding speed was determined on PAH-terminated monolayers, and PEMUs of up to 41 layers (FIG. 4). We found an enhancement of speed for PEMUs versus monolayer, probably due to reduced interaction with the underlying glass.

Biological Motors

The biologically-based components of the actuator comprise a first interactive biological material and a second interactive biological material. Each biological material is preferably a protein. Preferably the first interactive biological material is myosin and the second interactive biological material is actin. Alternatively, the first interactive biological material is microtubule (tubulin) and the second interactive biological material is kinesin or dynein. The interaction of the two interactive biological materials causes the movement of the member, e.g., a rod that has myosin on a portion thereof along its longitudinal axis, which movement may be unidirectional or bidirectional.

In operation, the second interactive biological material, e.g. actin, is associated with a source of energy to convert the second interactive biological material into a modified energy state (e.g. the actin is heated, electrochemical release of calcium ions or cleavage of a activate phosphate bond) so that it interacts with the first biological material to cause the movable member to move relative to a starting position. In the absence of the source of energy, i.e., when not heated, the second interactive biological material is inert, i.e., the material is incapable of causing the movable member to move relative to its starting position. The interaction of the two interactive biological materials is promoted by a substance that is source of chemical potential energy, such as a nucleotide such as adenosine triphosphate (ATP) or 2'-deoxy ATP. Other regulatory proteins such as troponin or tropomyosin may also be present. For example, with myosin and actin in the sample environment with ATP, myosin converts ATP hydrolysis into motion via its interaction with actin.

While the myosin deposited on the rod may be obtained from commercial sources, or from a variety of muscle sources, myosin from rabbit skeletal muscle or rat heart is useful. Methods of purifying myosin and HMM from animal tissue is well known in the art. See, e.g., Köhler, et al. Physiological Genomics 14:117–128 (2003); Liang, et al. Biophys. J. 85:1775–1786 (2003); Chase, et al. Am J Physiol Cell Physiol 278:C1088–C1098 (2000); or Gordon, et al. Biophys. J. 72:1295–1307 (1997).

Preferably the myosin is extracted from cold-water-adapted fish, e.g. *fundulus heteroclitus*, so that the actuator can operate over a broad temperature range. Myosin and actin are readily obtained from a variety of muscle sources, e.g., from rabbit skeletal muscle and rat heart. Of these two, rabbit skeletal muscle myosin is faster under a given set of conditions and, more significantly for prototyping general-purpose devices, has proven to be reliable and durable.

One of the major advantages of biological motors in general is their ability to work at ambient temperatures, i.e., at temperatures that are low relative to conventional engines. A second advantage is the relatively high efficiency of biological motors.

Figure 5:
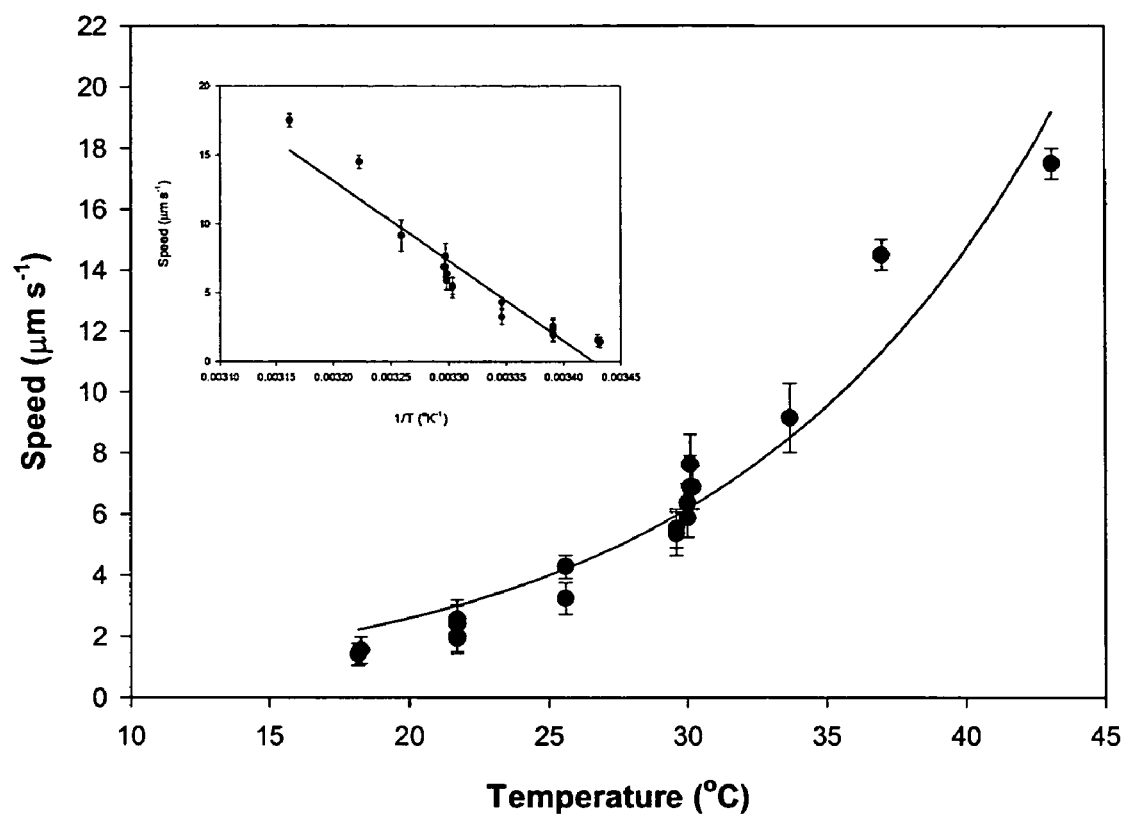
FIG. 5 illustrates the temperature dependence of in vitro motility using rhodamine-phalloidin labeled F-actin and HMM from rabbit skeletal muscle. The inset shows the data as an Arrhenius plot.

FIG. 5 shows, first, that the speed of motility of actin filaments driven by purified rabbit myosin is highly temperature sensitive. Second, the figure shows that there is no intrinsic limitation to operation at temperatures above 30° C. A third observation, which is closely related to the steep temperature dependence of speed, is the dramatic slowing of filament sliding at temperatures below 20° C. This observation is of clear practical importance for the actuators of the present invention.

The thermal sensitivity of function is an important design consideration for any practical nanoscale device based upon a biologically derived system. Rates of typical enzyme-catalyzed biological reactions typically double or triple with each 10° C. increase in temperature, meaning that a 40° C. range of ambient temperature might translate into an eighty-fold range in the rates of key reactions. In the absence of due consideration to this aspect of design, "real world" device function thus could be severely compromised by environmental temperature.

In mammals and birds, constant body temperatures avoid problems associated with the thermal sensitivity of biological reactions. Uniform cooling/heating of an assemblage of nanoscale actuators probably is not an attractive approach, however, because of the attendant energy cost and the complexity that this would add to the end product. It is preferable to have a device that can function well across a range of ambient temperatures, which means it must be based upon a form of myosin whose catalytic (and therefore motor) function has inherently low thermal sensitivity. Fortunately, natural selection has provided such a system.

Unlike mammals that maintain an essentially constant muscle temperature, many fish in their native habitat must be able to move not only in cold, deep water but also in warmer surface water. Extrapolated to the nanoscale, this is a highly desirable quality for actuators in devices that may be required to work in environments at the extremes of human habitability. There is good evidence that myosin purified from cold-adapted fish will be well-suited for use in nanoscale devices. Sliding speed of F-actin in the motility assay varied significantly less with temperature when myosin was obtained from carp acclimated at 10° C. versus 30° C. Chaen, et al., J. Biochem (Tokyo) 120:788–791 (1996).

*Fundulus heteroclitus* is a common minnow of the rocky intertidal and salt marshes of the eastern coast of the United States. Its life history includes frequent, acute changes in ambient water temperature that accompany the tides. The contractile protein complex of the musculature of this species is adapted specifically to maintain catalytic function and regulatory sensitivity to $Ca^{2+}$ over the range of naturally experienced temperatures. Sidell, et al., J. Comp. Physiol. 153:167–173 (1983). Further, its myofibrillar ATPase activity is relatively insensitive to changes in temperature across an unusually broad range of temperatures, from ~12° C. to at least 35° C. Id. With respect to protein stability and the thermal sensitivity of function, these are the same properties desired for a practicable linear actuator.

Actin can be obtained utilizing any well known method in the art. The invention preferably utilizes arrays of actin filaments, wherein the filaments in a single array maintain the same orientation. Actin filaments have a structural polarity. Most myosins move towards the "plus" end that is also referred to as the "barbed" end. The "plus" designation does not refer to electrical charge but rather the end having a faster rate of subunit addition.

Figure 6:
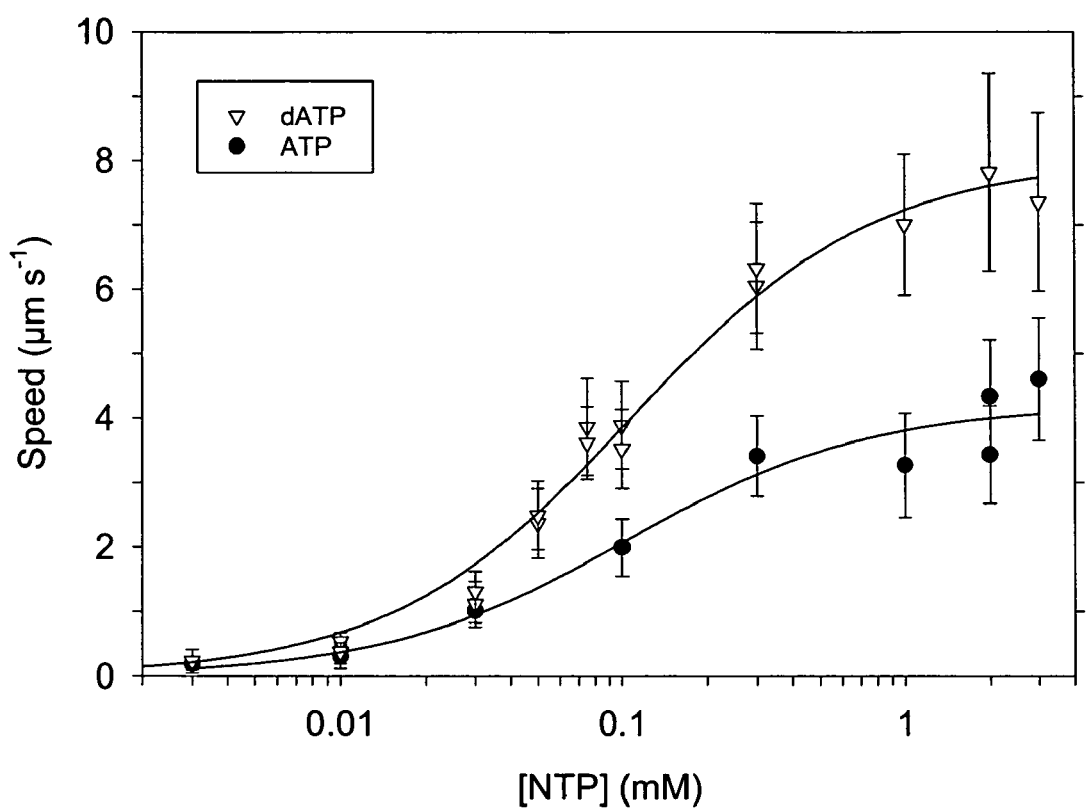
FIG. 6 demonstrates that in vitro motility speed is faster when 2'-deoxy ATP (triangles) replaces ATP (circles) as the substrate. Data were obtained with unregulated F-actin and rat cardiac heavy meromyosin.

The speed of actin filament sliding can be substantially increased by a variety of means other than increased temperature. First, replacement of ATP by 2'-deoxy ATP (DATP) substantially increased the rates of actin filament sliding when either rat cardiac myosin (FIG. 6) or rabbit skeletal myosin was the motor. Permeabilized muscle fiber assays substantiated this result by showing that unloaded shortening and the rate of isometric tension redevelopment were similarly increased in both muscle types. DATP is the adenine nucleotide that is normally incorporated into DNA and is not normally present at sufficiently high concentration in muscle cells to compete with ATP (which is at millimolar levels) for binding at the active site of myosin. The difference between ATP and dATP, as indicated by the name, is a single oxygen atom. These increased rates of actomyosin interactions due to such a small change in structure of the nucleotide substrate are not predicted from existing structural information about the myosin motor domain.

Figure 7:
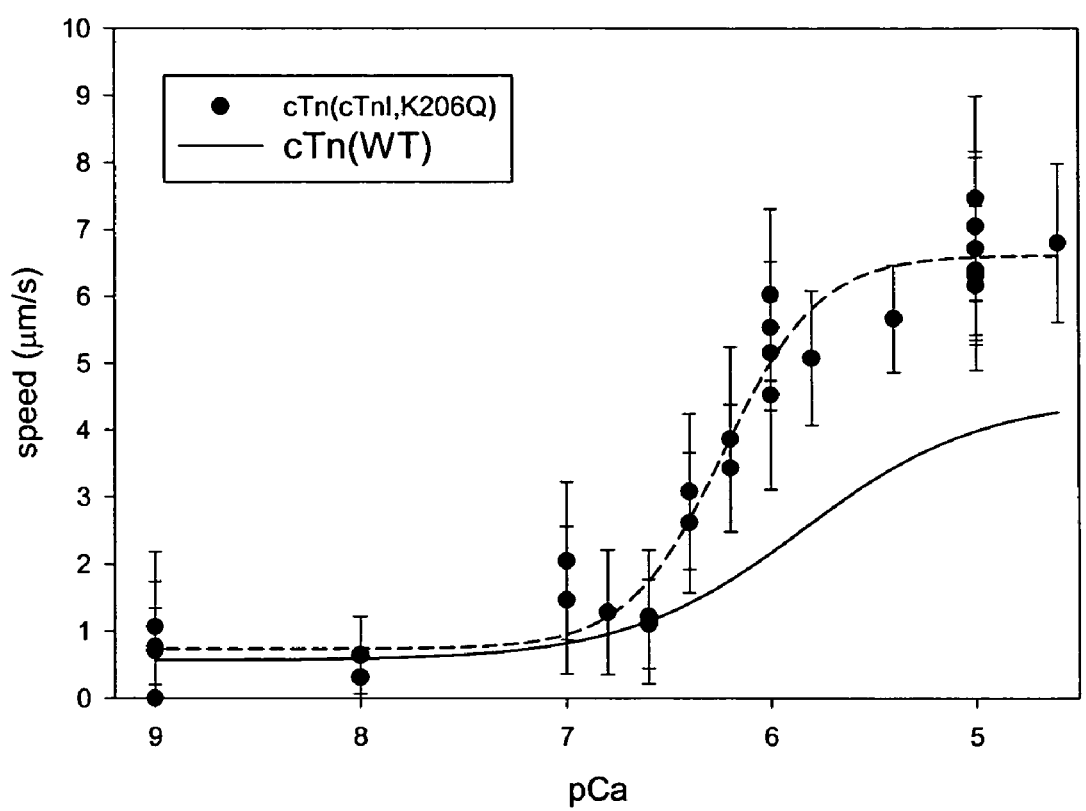
FIG. 7 depicts the enhancement of in vitro motility maximum speed by cardiac troponin containing hypertrophic cardiomyopathy mutant cTnI K206Q (circles, dashed line). Wild type cardiac Tn (solid line) does not enhance the maximum speed as compared with unregulated F-actin.

A second means of enhancing filament sliding speed is by adding regulatory proteins at elevated calcium concentrations. The calcium regulatory proteins troponin and tropomyosin bind to actin filaments and control actomyosin interactions in striated muscles by blocking interaction at low [$Ca^{2+}$] and permitting interaction, and thus force and/or filament sliding, at high [$Ca^{2+}$]. Troponin is a complex consisting of three protein subunits (TnC=calcium-binding; TnI=inhibitory; and TnT=tropomyosin-binding). Each troponin complex is associated with an α-helical coiled-coil tropomyosin dimer and seven actin monomers in the actin filament. Incorporation of troponin from rabbit skeletal muscle (or the equivalent proteins expressed recombinantly) increases the maximum speed (i.e., at high [$Ca^{2+}$] for regulated actin) measured in motility assays relative to unregulated actin. This effect is large—almost a twofold increase in speed. Cardiac troponin motility enhances filament sliding speed, but only when the TnI subunit contains specific mutations, e.g. lysine 206 to glutamine, that are associated with inherited forms of hypertrophic cardiomyopathy (FIG. 7). TnC and TnI subunits of troponin in the heart are synthesized from different genes in the heart and in fast skeletal muscle. Although the cardiac and skeletal isoforms of each subunit are similar, there are significant differences in sequence that are responsible for these (and other) functional differences.

Motility assays are carried out either with RhPh F-actin (unregulated) or with RhPh F-actin-TnTm (regulated) using a wide variety of conditions. We have tested four ionic strength (Γ/2) conditions: AB solution (0.045 MΓ/2); 0.085 MΓ/2; 0.115 MΓ/2; and 0.14 MΓ/2 and also a variety of partially non-aqueous conditions (e.g., DMSO) and solvents of altered viscosity. See, e.g., Chase, et al., Am. J. Physiol. Cell Physiol. 278:C1088–C1098 (2000). In all buffers for fluorescence imaging of RhPh labeled actin, 16.7 mM glucose, 100 μg ml$^{-1}$ glucose oxidase (Sigma, St. Louis, Mo.), 18 μg/ml catalase (Boehringer-Mannheim, Indianapolis, Ind.), and 40 mM DTT (BioRad, Hercules, Calif.) are added to minimize photo-oxidation and photobleaching. In motility buffers other than AB, the typical conditions are (mM): 2 MgATP, 10 EGTA, and 2.6 Mg$^{2+}$, with MOPS and K-propionate (KPr) added to adjust ionic strength (28–70 mM and 65 mM, respectively at 0.085 MΓ/2; 88–128 mM and 100 mM, respectively at 0.115 MΓ/2; and 155–194 mM and 133 mM, respectively at 0.14 MΓ/2). Typical pH is 7.0 at 30° C. and appropriate amounts of CaPr$_2$ are added to obtain PCa's between 9.2 and 4.0. Methylcellulose (MC) is added to assay buffers (0.4% MC, typically, or 0.7% MC for control experiments at 0.085 MΓ/2; 0.6% or 0.7% MC at 0.115 MΓ/2; and 0.7% MC at 0.14 MΓ/2) to prevent F-actin diffusion from the assay surface at elevated Γ/2; MC is prepared as a 2% wt/vol concentrated stock solution by dialysis against 1.5 mM NaN$_3$ and volumes of this highly viscous solution are measured using a positive displacement micropipettor (Labindustries, Berkeley, Calif.) to ensure accuracy. Motility assay solutions other than AB are typically mixed as 2× concentrated stocks and stored as frozen aliquots until use; immediately prior to each assay, MGATP, anti-bleaching agents, MC, TnTm (where required) and an appropriate volume of water are added to dilute the motility buffer to the correct concentration.

Previous analyses of filament motion were obtained from analysis of centroids using hardware and Expert Vision software from Motion Analysis Systems (Santa Rosa, Calif.). Data are acquired both in real-time during experiments and most often from videocassette recordings. For most assays, filament outlines (obtained using hardware edge-detection) are sampled by the Motion Analysis system at 10 frames per second (fps) for 60 s (higher frame rates can be used for substantially faster motion and slower frame rates or smoothing for slower motion) and individual filament paths are retained only when the filament centroid can be unambiguously tracked for a minimum of 2 s.

Speed statistics are calculated for each filament centroid that can be unambiguously tracked along its path for at least 2 s, and the ratio of S.D. to mean speed ($r_u$) is calculated as an indicator of uniformity of motion. A filament is considered to move uniformly if $r_u<0.5$ for 10 fps sampling (or if $r_u<0.3$ for 2 fps sampling; see below). The fraction of uniformly moving filaments ($f_u$) is defined as proportion of filament paths meeting the criterion for uniform motion. The mean speed ($s_u$) is calculated as the unweighted mean of mean speeds from those filament paths that met the criterion for uniform motion.

When $s_u$ is <5 μm s$^{-1}$, the centroid position data are further processed to reduce the contribution of spurious, apparent high speed measurements which result from pixel jitter in the edge detection hardware. First, the centroid position versus time data in each filament path are smoothed using a five-point moving average filter (equal weights). Then a subset of the data are retained to yield an effective sampling rate of 2 fps. To complete the analysis of smoothed data, further processing is as described above for un-smoothed (10 fps) data except the criterion for uniform motion is made more stringent ($r_u<0.3$ for 2 fps data).

Utilizing the invention, it is possible to avoid the foregoing optical methods of following motion of actin filaments. Rather, the actuator and Hall gradiometer of the invention can magnetically sense movement of a myosin coated member.

Energy Transmission

A further aspect of this invention provides a well structure for use in the biomolecular-based actuator. The well structure comprises at least one array of protein filaments positioned to interact with a protein coat on a movable member having a biocompatible molecular layer deposited on the surface of the member, where the protein coat adheres to at least a portion of the biocompatible molecular layer;

an energy-transmitting stripe associated with the array in a manner to selectively energize the array;

a well containing a substance of chemical potential energy that aids the interaction of the protein coat on the member with the array, the well being positioned to retain the substance in contact with the array and the protein coat;

a hydrophobic region positioned on opposite sides of the well to retain the substance within the well while the member is slidingly engaged.

Preferably the energy-transmitting stripe is a platinum, nickel or gold stripe that is about 10 nm to about 250 nm thick (height off the surface) and at least about 10 nm wide. The width of the stripe is the dimension parallel to the actin filaments associated with the stripe and can be as large as microns to 10's of microns, i.e., the length of typical actin filaments. Ideally, the energizing stripe will be insulated electrically, but not thermally, from the surrounding solution.

As discussed previously, the preferred substance of potential chemical energy is adenosine triphosphate (ATP) or 2'-deoxy ATP. Generally, consistent with the previous disclosure, the array is an array of actin filaments, the protein is myosin deposited on a rod, two separate parallel arrays of actin filaments are aligned along the same axis but with opposite polarities, each array of actin filaments positioned to interact with the myosin coating, and a separate energy-transmitting stripe associated with each array of actin filaments in a manner to selectively energize an actin filament array so that when one of the energy-transmitting stripes is sufficiently energized, the actin/myosin interaction is such that the rod is moved from its starting position in a direction perpendicular to the actin filament.

The well is prepared by providing a reservoir having an inside surface and two orifices; positioning at least one array of a protein on the inside surface of the reservoir; positioning an energy-transmitting stripe in contact with the array so that the end of the stripe away from the protein array may be connected to an energy source; and providing a hydrophobic region at each orifice to provide a seal for aqueous liquid when placed in the reservoir and allow a movable member to slidingly engage the well through each orifice. The array of a protein is preferably an array of actin filaments wherein two separate, parallel arrays of actin filaments are aligned along the same axis but with opposite structural polarities and are positioned on the inside surface of the reservoir but spaced from each other and a separate energy-transmitting stripe contacts each array in a way to selectively energize an actin filament array. The actin filaments within the parallel actin arrays positioned to be parallel to the longitudinal axis of a movable member, e.g., a rod, that would be positioned through each orifice.

In a preferred embodiment two separate, parallel arrays of actin filaments are aligned along the same axis but with opposite structural polarities and both arrays are positioned to interact with myosin that is coated on the movable member, e.g., a rod. A separate energy-transmitting stripe is associated with each actin array in a manner to selectively energize an actin array so that when one of the stripes is sufficiently energized, the actin/myosin interaction is such that the moveable member is moved from its starting position in a direction parallel to the actin filaments within the arrays. The energy-transmitting stripe may transmit heat, electricity, light, or electrochemical energy. Preferably the stripe is a stripe that transmits heat, e.g., platinum about 2 nm to about 10 nm wide and about 10 m to about 250 nm thick. When the movable member is a rod, the actin filaments within the parallel actin arrays are parallel to the rod's longitudinal axis, such that the rod is moved in the direction of its longitudinal axis.

Hall Gradiometer

Figure 8:
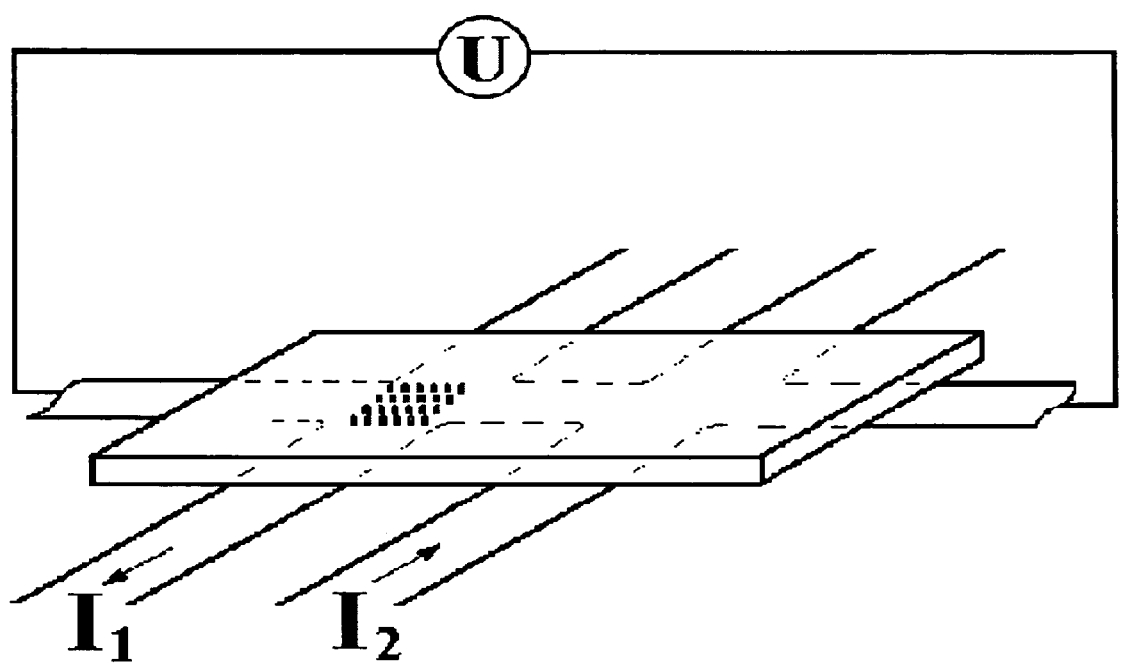
FIG. 8 provides a schematic diagram depicting Hall gradiometry.

The two dimensional electron gas formed in a semiconductor heterostructure is one of the cleanest electronic systems. The combination of low electron density and high mobility results in a large and measurable Hall response to magnetic field and makes such structures sensitive magnetic field detectors. A Hall gradiometer consists of two Hall crosses made out of a semiconductor heterostructure, as shown in FIG. 8. The currents in the two crosses flow in opposite directions so that they yield an exact cancellation of the background Hall signal due to an applied field. This enables the detection of the tiny dipole field generated by small number of magnetic nanoparticles on one of the crosses. This method has been widely applied to measure magnetization of arrays of ferromagnetic or superconducting nanoparticles, larger individual disks, and the fringe field at the end of a nanorod. Because only those particles that lie inside the active area of the Hall cross contribute to the effective Hall signal, the size of the Hall cross must be tailored to match the size of the array or other magnetic sample in order to maximize the device sensitivity.

The present invention provides a combination of a Hall gradiometer with an actuator having a movable member that moves as a result of biomolecular interaction of a biologically-based components within the actuator, wherein the movable member has a magnetic field associated with it so that the motion of the movable member is detected by measuring the fringe magnetic field of the movable member in the gradiometer. The gradiometer/actuator is designed to optimally operate at temperatures of about 0° C. to 70° C. The advantage of using the actuator of the invention with a Hall gradiometer is the small size of the actuators of the invention. Thus the combination can have dimensions of less than one centimeter in any direction.

The combination can incorporate a feedback mechanism between the gradiometer and the actuator, so that the feedback signal can be used to improve accuracy and speed of actuator motion. The combination of Hall gradiometer and actuator and further be interactively connected to at least one other combination, e.g., a sensor that would activate the actuator when an abnormal condition is encountered in the environment. Additionally, the combination of Hall gradiometer and actuator can be combined with a fluid-containing reservoir, wherein the movable member of the actuator acts as a valve to release fluid from the reservoir.

Figure 9A:
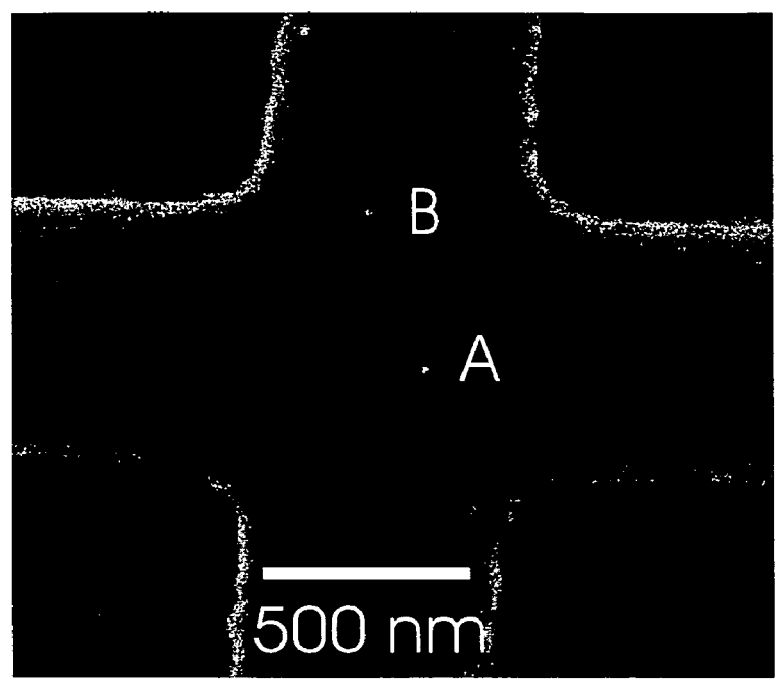
FIG. 9A illustrates a Hall cross with a single particle in its active region.
Figure 9B:
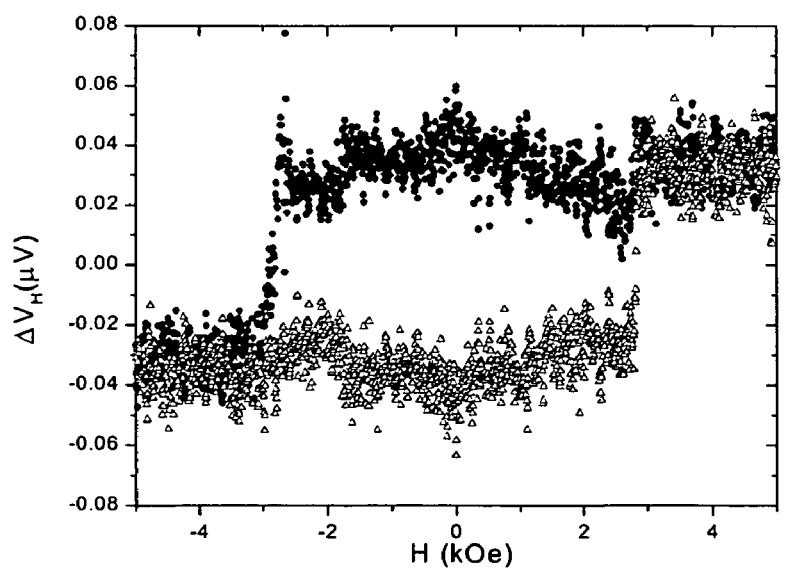
FIG. 9B illustrates the Hall voltage due to this particle, showing hysteresis with sharp switching.

The present invention permits one to decrease the size of the Hall gradiometers in order to measure a single Fe particle down to a 10 nm diameter. Electron beam lithography and wet chemical etching were used to pattern the Hall gradiometer and STM-assisted micro-CVD to grow Fe nanoparticles with precision alignment. FIG. 9A shows a Hall cross ~500 run in size and a single particle in the active region of the Hall cross. FIG. 9B shows the Hall voltage due to the single Fe particle, displaying a hysteresis loop with sharp switching behavior expected of a uniform ferromagnetic particle. These Hall gradiometers have a sensitivity to detect ~$10^5$ spins, approaching that of the best micro-SQUID (Superconducting QUantum Interference Device), but with much wider operational temperature and field range.

The Hall gradiometer is an ideal choice for magnetic bio-sensing: it combines the advantages of ambient operation of GMR (Giant MagentoResistance) sensors and the high magnetic and spatial sensitivity of micro-SQUIDs. The present invention permits detection of magnetic particles far smaller than 100 nm and spatial resolution on the order of 10 nm. The spatial resolution far exceeds that for optical fluorescent method which is limited to the wavelength of the light used. With the Hall gradiometer of the invention, at least an order of magnitude smaller magnetic particles than previously used can be attached and detected, further reducing the load and perturbation to the intrinsic motion of the biomotors.

EXAMPLES

The following examples are given to provide representative compositions and methods included as part of this invention. Throughout the examples chemical formulas will be used to name compounds (e.g. $NaHCO_3$ is sodium bicarbonate) as appropriate.

Example 1

Purification of Myosin

Myosin from *Fundulus heteroclitus* is prepared by the method of Margossian and Lowey (1982) with minor modifications. *F. heteroclitus* (6–8 individuals) are euthanized in seawater containing MS-222 and placed on ice for 20 minutes to reduce actomyosin complex formation. Fast glyocolytic myotomal muscle is dissected and immediately used to isolate myosin. Muscle is coarsely chopped and homogenized in 3 volumes of 0.3M KCl, 0.15M potassium phosphate (pH 6.5), 1 mM EGTA, 1 mM DTT, and 5 mM ATP using a Tissumizer (Tekmar, Cincinatti, Ohio). Muscle homogenate is extracted for 10 minutes at 4° C. with constant stirring and then diluted 4-fold with cold water to stop the extraction. This suspension is filtered through sterile cheese cloth, and myosin is precipitated by diluting the mixture 3-fold with cold water containing 10 mM DTT. The precipitate is allowed to settle 2.5 hours to overnight at 4° C., and the supernatant is discarded. The precipitated protein is centrifuged at $5000 \times g_{avg}$ for 10 minutes at 4° C. The pellet is dissolved in 2M KCl and then diluted to 0.3M KCl with ATP (dissolved in water) to reach a final ATP concentration of 5 mM. The ionic strength at this point is not allowed to fall below 0.3 to keep myosin in solution while precipitating actomyosin. The sample is centrifuged at $118,000 \times g_{avg}$ for 45 minutes at 4° C. The supernatant is diluted 20-fold with cold water and is allowed to precipitate overnight at 4° C. The supernatant is drawn off and the precipitated myosin is centrifuged at $7800 \times g_{avg}$ for 15 minutes at 4° C. Myosin pellets are dissolved in myosin storage buffer (0.5M KCl, 10 mM $Na_2PO_4$, pH 7.0, 2 mM $MgCl_2$, and 1 mM DTT). Myosin concentration is determined using an extinction coefficient of 0.53 $cm^{-1}$ at 280 nm, and 520 kD molecular weight. Myosin is stored in glycerol (1:1) at −20° C. for 4–6 weeks.

Expression of Troponin Subunits

Recombinant troponin subunits were expressed in *E. coli* and mutated essentially as described for TnC. Dong, et al., J. Biol. Chem. 271:688–94 (1996). To obtain clones of rat cardiac troponin subunits for studies involving mutagenesis, total RNA was isolated from adult rat cardiac muscle by the guanidinium isothiocyanate method of Chomczynski and Sacchi (Anal. Biochem. 162:156–9 (1987)). First strand cDNA was synthesized using the method of Saiki et al. (Science 230:1350–4 (1985)). The product of first strand cDNA reaction was then directly used in the polymerase chain reaction (PCR) to synthesize Tn subunit ds cDNA with a pair of primers constructed according to the previously published cDNA sequences. PCR products were purified using 1% low melting point (LMP) agarose gel (GIBCO BRL). To ensure proper digestion by restriction enzymes the purified PCR products were cloned into a TA cloning vector pCR 2.1 (Invitrogen) followed by the standard procedures for transformation and propagation of the recombinant molecules in an *E. coli* host. The recombinant DNA molecules were then purified from bacterial cells and digested by the selected restriction enzymes. The digested cDNA was again purified by LMP gel and subcloned into a pET-24 expression vector (Novagen) for sequence analysis. Sequenase Version 2.0 DNA Sequencing Kit from United States Biochemical (USB) was used to carry out DNA sequence analysis.

cDNAs were expressed using a vector pET-24 (Novagen) containing the T7 promoter, lac operator, and a kanamycin resistance gene. The purified rat cTnI cDNA digested with the restriction enzymes was ligated into the polylinker sites of pET-24. The recombinant DNA was then transformed into a cloning strain HMS 174 (Novagen). Transformed cells were grown on LB agar plates in the presence of kanamycin. Colonies were screened for inserts by digestion with the restriction enzymes. This procedure allowed us to check the insert DNA prior to transforming recombinant plasmid into an expression host. After a positive clone was identified, the recombinant DNA (vector plus target gene) was subsequently transformed into the host strain BL21(DE3) lysogen (Novagen). Transformed cells were grown on LB agar plates in the presence of kanamycin. A single colony was picked and was inoculated into LB medium containing kanamycin at 37° C. until the OD600 reaches 0.8 absorbance units. IPTG was then added to a final concentration of 1 mM to induce the expression of target protein. The induced culture was incubated for at least 3 more hours and harvested by centrifugation. The cells were washed once with 50 mM Tris (pH 8.0), 2 mM EDTA and then resuspended in a solution containing 2.4M sucrose, 1% Triton X-100, 50 mM Tris (pH 7.0), 10 mM EDTA, 1 mM DTT, and 0.5 mg ml-1 lysozyme. The cell suspension was placed on ice for 60 min and then sonicated for 5 min. The solution was centrifuged at 12,000×g for 20 min at 4° C. An equal volume of 2×SDS sample buffer was added to an aliquot of sample from the supernatant for SDS☐PAGE analysis. Recombinant proteins were purified from the supernatant as described above for native troponin subunits. Mutants are made by site-directed mutagenesis using T7-GEN In Vitro Mutagenesis Kit (United States Biochemical). The mutant proteins are expressed with the pET system and purified, analyzed and stored as for WT proteins.

Troponins containing recombinant subunits are obtained by recombining WT cTnC, WT cTnT, with either WT cTnI or mutant cTnI according to Potter (Methods Enzymol. 85:241–263 (1982)). The MW and extinction coefficient used were the same as for native Tn. Tn complex is stored frozen in Tn exchange buffer (−80° C.). The stoichiometry of recombinant protein incorporation into representative sample preparations will be evaluated by SDS-PAGE.

Example 2

Motility Assay

The in vitro assay is conducted in a "flow cell" which consists of a microscope slide, acid-washed coverslip and glass spacers all held together (and made watertight on two of four sides) by vacuum grease (see FIG. 4 in Kron, et al., Methods Enzymol. 196:399–416 (1991)). Specifically, flow cells are constructed on conventional, clear glass microscope slides with #1 coverslips resting on $\#1^{1/2}$ thickness glass spacers held in place with silicone high vacuum grease (Dow Corning, Midland, Mich.). Coverslips are coated with a thin layer of nitrocellulose (Ernest Fullam, Latham, N.Y.) freshly diluted to 0.1% in amyl acetate, and are used the same day. Total chamber volume is typically 40–50 μl.

Solutions are added to the flow cell in an order similar to that described by Homsher et al. Biophys. J. 70:1881–1892 (1996) and Gordon et al. Biophys. J. 72:1295–1307 (1997). First, HMM is added for 1 min, followed by "actin buffer" (AB: 25 mM KCl, 25 mM imidazole, 4 mM $MgCl_2$, 1 mM EGTA, 1 mM DTT, pH 7.4) plus 0.5 $ml^{-1}$ BSA for 1 min to block non-specific protein binding. After washing the chamber with AB, unlabeled F-actin (1 mg $ml^{-1}$; sheared by about 15 rapid passages through a 23 gauge needle) is added for 1 min. The chamber is washed with AB, AB with 0.5 mM ATP, and again with AB. This procedure uses unlabeled F-actin to block ATP-insensitive heads on HMM that either were not removed in an earlier centrifugation step or were formed when HMM bound to the nitrocellulose surface. Dilute rhodamine-phalloidin (RhPh) labeled F-actin (unregulated actin) or RhPh F-actin-TnTm (regulated actin) is added to the chamber for 20 s or 1 min, respectively, and is washed with either AB alone or other rigor buffer (no ATP) plus appropriate concentrations of Tn and Tm, respectively. Finally, the assay buffer is infused into the flow cell and the slide was transferred to the microscope stage.

Fluorescence microscopy is carried out on a Diastar upright microscope (Leica, Deerfield, Ill.) equipped with a 100 W Hg arc lamp. The flow cell temperature is maintained at about 30° C. by circulating water through a copper coil wrapped around the 100× objective. The baseline experimental temperature can be changed simply by changing the temperature of the circulating water bath. RhPh F-actin and RhPh F-actin-TnTm filaments are imaged with a SIT camera (Dage-MTI model VE 1000, Michigan City, Ind.) and recorded with a time-date generator signal (model WJ-810, Panasonic, Japan) on VHS videocassettes (VCR model AG7350, Panasonic, Japan).

Example 3

PEMU Coating and Motility Assay

Microscope cover slips (18×18×0.15 mm) were cleaned in "piranha" (70% $H_2SO_4$(conc)/30% $H_2O_2$: caution, piranha is a strong oxidizer and should not be stored in closed containers). Poly(styrene sulfonic acid), PSS, (molecular weight 5×10$^5$) and poly(allylamine hydrochloride), PAH, (molecular weight 7×10$^4$) were used as the polyanion and polycation, respectively. Both solutions were prepared in imidazole buffer (0.025 M, pH=7.4). Polymer solution concentrations were 0.01 M (quoted with respect to the monomer repeat unit). A robotic platform (nanoStrata Inc.) exposed the cover glass alternately to the two polymer solutions for 5 minutes with three rinses of imidazole buffer in between each lasting for 1 minute. Rinse and polymer solution volumes were approximately 50 mL each. Surface compositions ranged from a monolayer of PAH to multilayers of up to 41 alternating layers of PAH and PSS with PAH always being the top layer. Prior to use, PEMUs were annealed in 1.5M NaCl for 3 h to produce a smooth surface[27]. Atomic Force Microscope (AFM) scans showed the RMS surface roughness of multilayers to decrease from 4.0±0.3 to 1.0±0.4 nm following this procedure.

Cover slips were then placed in a flow cell and an in vitro actomyosin motility assay was performed, as previously described. Kron, et al., Methods Enzymol. 196:399–416 (1991) and Chase, et al., Am. J. Physiol. Cell Physiol. 278:1088–1098 (2000). Rabbit skeletal muscle heavy meromyosin prepared in imidazole buffer with a pH of 7.4 will have a net negative charge, thus its adsorption on the positively charged PAH surface is facilitated. Nonspecific protein binding sites were blocked with BSA after application of rabbit skeletal muscle heavy meromyosin. Assays were conducted with AB solution (25 mM KCl, 25 mM imidazole, 4 mM $MgCl_2$, 1 mM EGTA, 1 mM DTT, pH 7.4). Motility buffer was AB plus 2 mM ATP, 0.3% methylcellulose, 16.7 mM glucose, 100 $\mu$g/ml glucose oxidase, 18 $\mu$g/ml catalase and an additional 40 mM DTT plus modifications described below for specific experiments. Sliding RhPh-labeled actin filaments at 30° C. were recorded on videotape by epifluorescence microscopy. Movement of essentially all actin filaments occurred on both mono- and multilayers. Quantitative analysis of filament motion was difficult, however, because filaments were much shorter (average length 1.12±0.12 $\mu$m, N=50) than typically observed with nitrocellulose-coated surfaces, suggesting that some feature of the surface was causing filaments to break up. The length of the actin filament is important not only because of detection limits, but also because it limits both the potential cargo that might be transported and the ability to control its movement.

Figure 10:
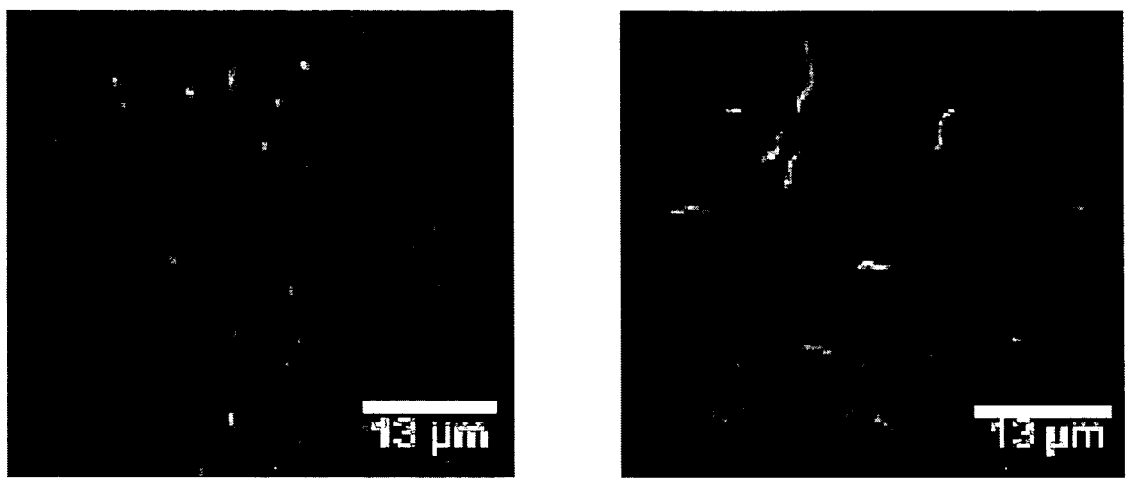
FIG. 10 illustrates actin filaments on a PAH terminated multilayer without (left panel) and with (right panel) addition of 0.6% Triton X-100 to the HMM solution.

To minimize filament breakup, the nonionic surfactant Triton X-100, was added to HMM solution at a concentration of 0.6% when it was incubated with the PAH surface. The average sliding speed remained the same (2.7±0.01 $\mu$m/sec and 2.9±0.08 $\mu$m/sec without and with the addition of Triton X-100 respectively), but filament length was comparable to that obtained on a nitrocellulose surface with an average length of 7.5±3.6 $\mu$m. (FIG. 10).

Filament sliding speed was determined on PAH-terminated monolayers, and PEMUs of up to 41 layers (FIG. 4). We found an enhancement of speed for PEMUs versus monolayer, probably due to reduced interaction with the underlying glass. Filament sliding speed was faster on the multilayer surface, with a speed of 3.4±0.03 $\mu$m/s (N=27) compared to 2.7±0.1 $\mu$m/s (N=22) on the monolayer surface. For reference, the sliding speed on a nitrocellulose surface under our conditions was 3.3±0.1 $\mu$m/s (N=20). These measurements were done with 0.0145M KCl in the motility buffer.

Figure 11:
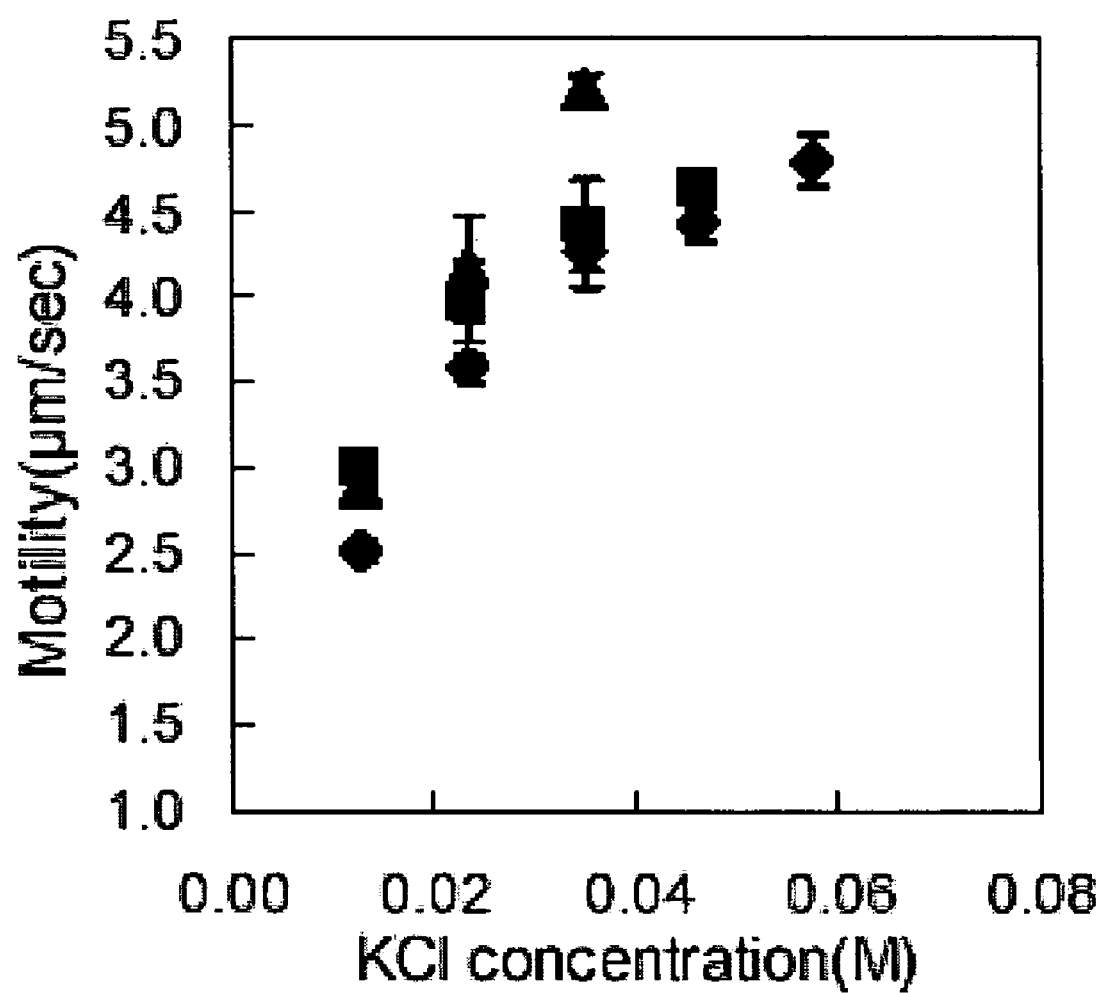
FIG. 11 depicts the effect of salt concentration of the buffer on the average speed of actin filaments on a PAH terminated PEMU (11 layers) (triangles), nitrocellulose (squares) and PAH monolayer (diamonds).

The motility buffer was prepared with a range of KCl concentrations. At low salt concentrations the speed of actin on the multilayer surface was comparable to that on a conventional nitrocellulose surface, whereas actin moved slightly more slowly on a PAH monolayer (FIG. 11). As the salt concentration was increased, motion was faster on multilayer surfaces compared to nitrocellulose. However at salt concentrations above 0.06M filaments dissociated from the surface and diffused into the motility buffer solution.

Electrostatic interactions are important for formation of the actomyosin complex. Electrostatic interactions of these proteins with the surface are also possible although such nonspecific interactions should have been blocked (by BSA and by sheared, unlabeled F-actin) during manufacture of the flow cell. Increasing the salt (KCl) concentration of the motility buffer weakens these interactions, as a result the actin filaments will slide more smoothly and their speed is greatly enhanced.

Figure 12:
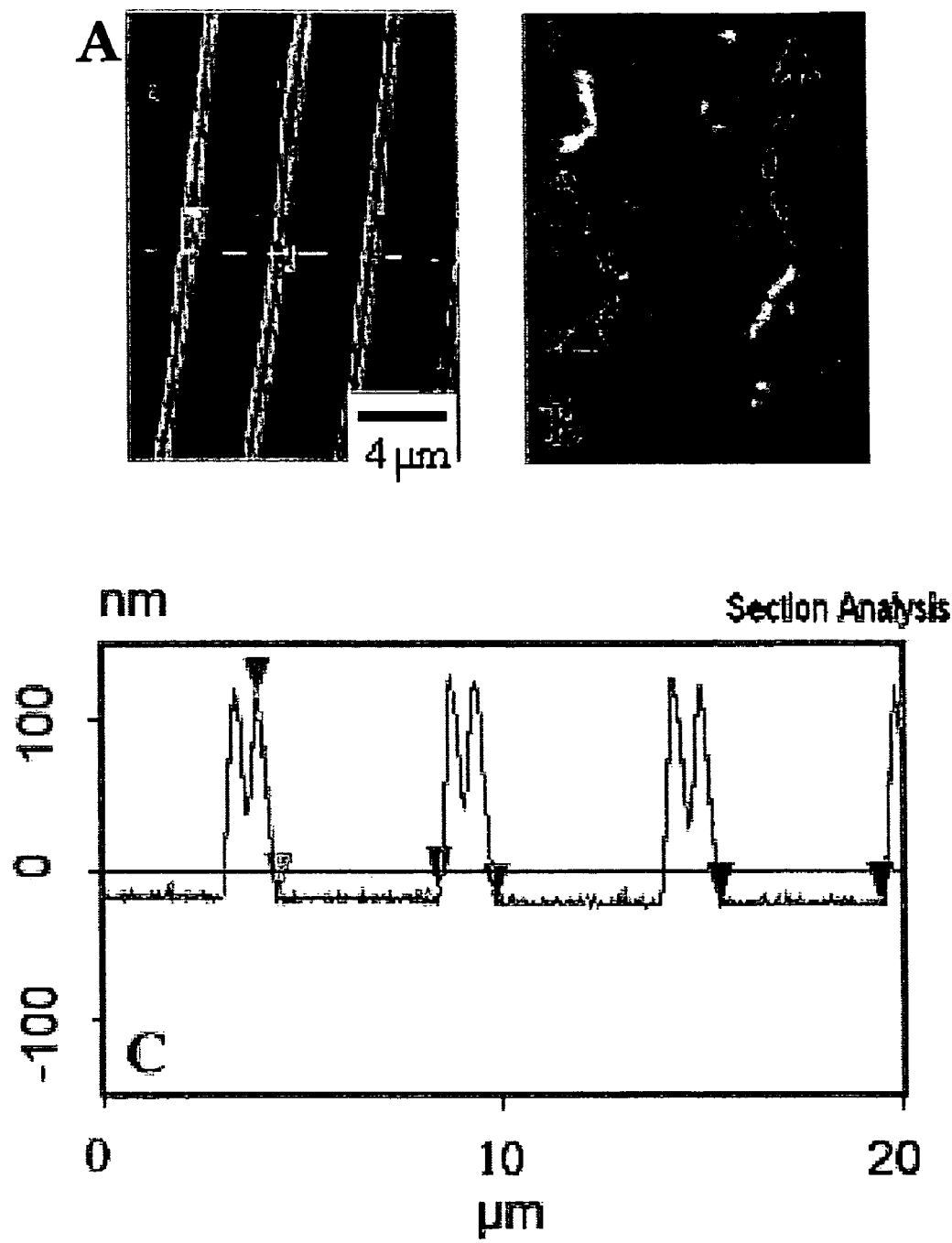
FIG. 12 illustrates AFM scans (FIG. 12A) and section analysis (FIG. 12C) of a stamped multilayer surface, showing a pattern with barriers of PEBSS 1.44 μm wide and 132.28 nm height.

The polymer (2.5 wt. % PEBSS in a mixture of ethanol, propanol, dichloromethane and tetrahydrofuran) was applied to the surface of the stamp with a cotton swab. The stamp was then pressed for 7 sec on the top of the multilayer. FIG. 12 shows the well defined channels, with PEBSS walls >100 nm high, that were obtained. Sliding actin filaments were observed only within the channels; no actin filaments, moving or immobile were observed on the PEBSS walls (FIG. 12B) suggesting that functional HMM bound only to PAH on the floor of the channels. Filaments were divided into three categories according to length. The "long" (longer than the channel width 9.3+0.8 $\mu$m) and "medium" (approx. as long as the channel width 4.5±0.5 $\mu$m) filaments remained inside the tracks with no change in lanes or direction (U-turns). Actin filaments rebounded efficiently off walls and remained inside the channels, consistent with measured persistence length of 18 $\mu$m for phalloidin stabilized F-actin. During an observation period of 26 seconds, a small proportion of filaments (11.5%, N=35) were observed to diffuse into solution. In the case of short filaments (shorter than the channel width 1.66±0.1 5 $\mu$m), 40% of the filaments maintained the same direction (N=35).

Example 4

Figure 13:
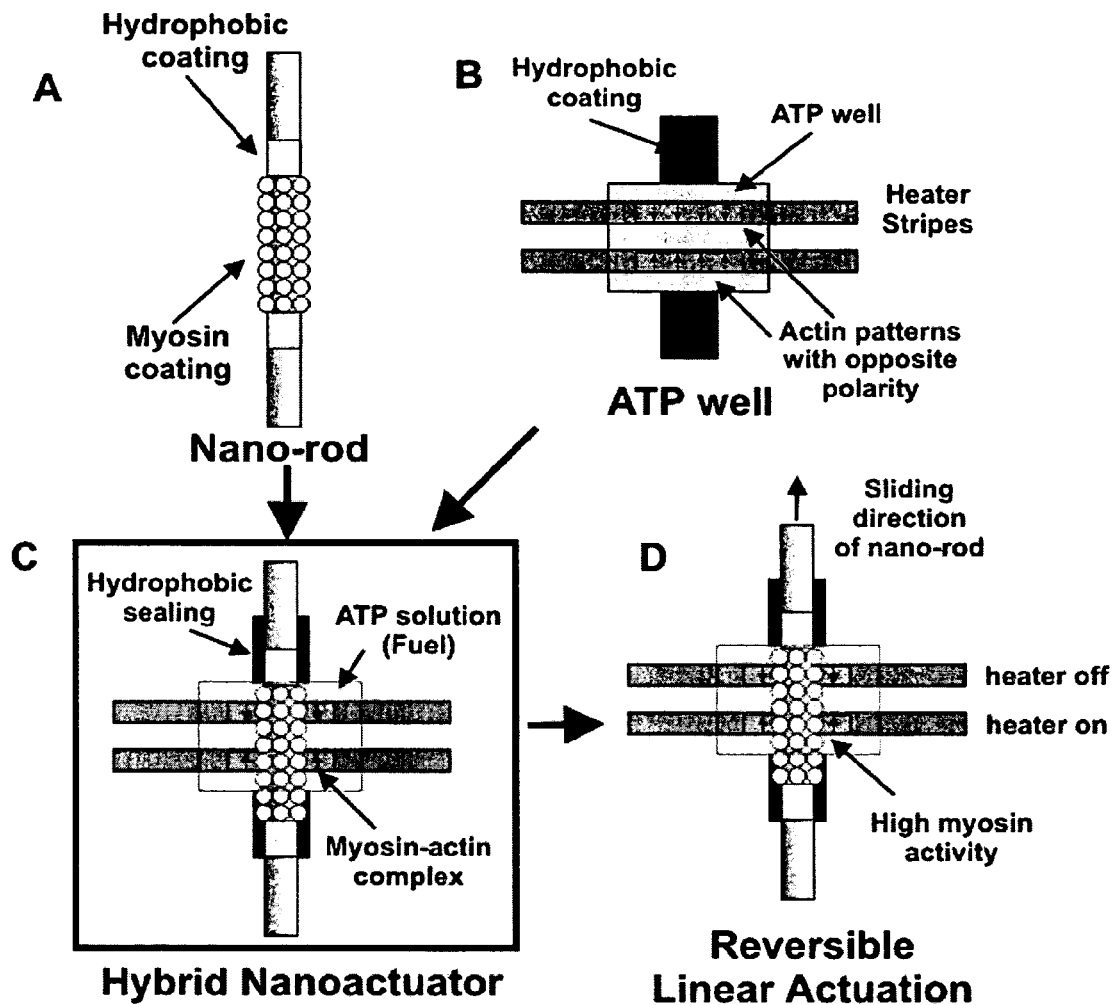
FIG. 13 illustrates a nano-actuator of the invention.

Turning now to FIG. 13, one sees various aspects of the invention in a specific example. In FIG. 13A, one sees a rod referred to as a nano-rod which has a hydrophobic coating with a myosin coating circumscribing a portion of the rod. One also sees a representation of the well that is part of the actuator of the invention where there is a hydrophobic coating region which would provide for snuggly fitting around the rod as it would be inserted into the well. The well holds, e.g. ATP to aid in the interaction between the myosin coated on the rod and the actin which is coated in the reservoir into which the rod fits. Thus, the rod would slide through the hydrophobic coating area of the two orifices in the well whereupon the parallel actin arrays, shown as actin patterns with opposite polarity as indicated by the arrows, are shown to be parallel to each other and aligned such that the actin filaments within the arrays are parallel to the longitudinal axis of the rod. In FIG. 13C one sees a representation of the rod in combination with the well to form the actuator of the invention. The ATP solution is viewed as the fuel for running the actuator. The hydrophobic regions seals the ATP in the reservoir and the interaction then is between the myosin and the actin with the heater on the lower actin array, the rod will move in a direction of the longitudinal length of the rod. While the actuator is shown as a reversible linear actuator in that there are two arrays of actin shown and thus it is reversible, that is, bidirectional, it can be designed with only one actin array which would make it a monodirectional unit. In this case, the reversible linear actuation is controlled via temperature on the stripe which is preferred to be a platinum, nickel or gold stripe, shown as a heater stripe. While the heater stripe is preferred, the stripe may transfer to any form of energy that can aid in the interaction between the material on the rod i.e. myosin and the material in the well, i.e. actin.

Example 5

Reversible Linear Nano-Actuator

Figure 14:
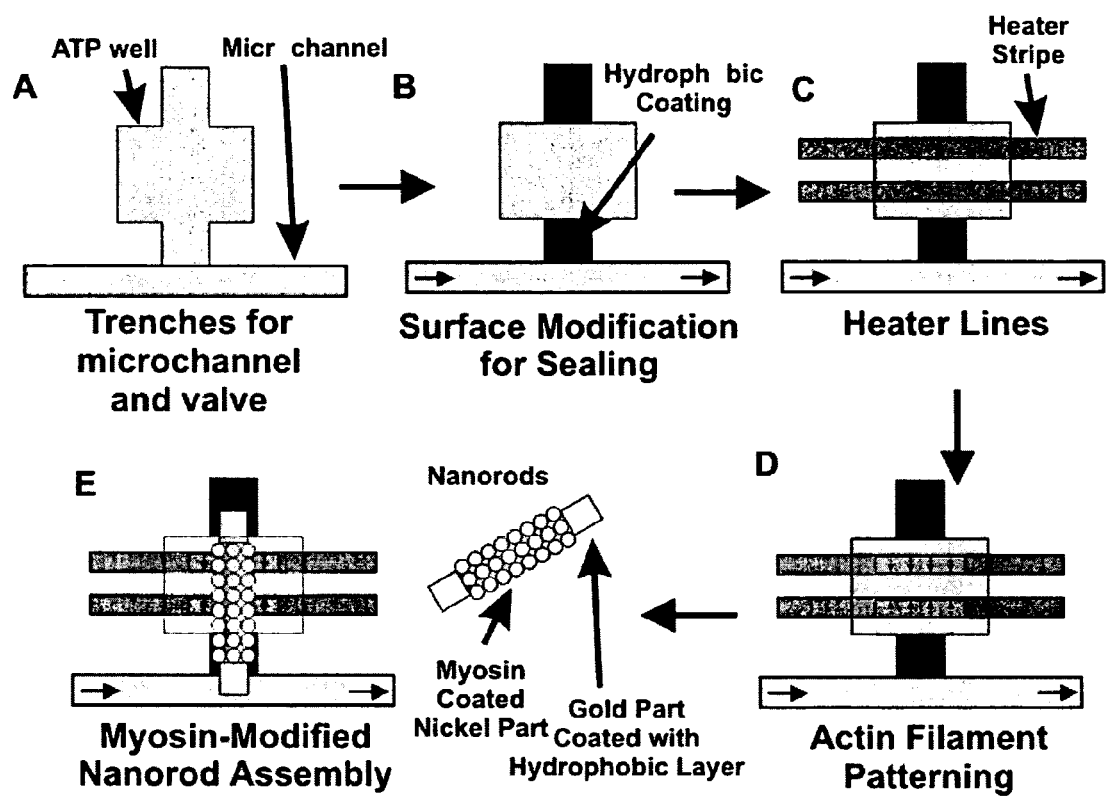
FIG. 14 provides a schematic diagram depicting a valve system utilizing an actuator of the invention.

FIG. 14 shows an application of the actuator of the invention as a valving mechanism for microchannel system in a bioanalysis chip. As a first step, trenches which defines the valve and microchannel are fabricated via microfabrication method on a solid substrate and the trench surface will be coated with hydrophilic molecules (FIG. 14A). Then, the bottleneck between the valve and microchannel is coated with hydrophobic molecules (FIG. 14B) to prevent possible leakage of ATP solution for the actuator into the microchannel. Then, two heater lines are fabricated in the valve via microfabrication method (FIG. 14C). The surface of each heater line is coated with actin filaments layer with opposite polarity via (FIG. 14D). The nanorods are prepared so that they have gold part at both ends and nickel in the middle. First gold parts are coated with 1-octadecanethiol molecules to achieve hydrophobic properties and then nickel is coated with myosin. The rods are assembled onto the actuator trenches (FIG. 14E). The strong interaction between myosin and actin as well as hydrophobic interaction between rod and hydrophobic coating on the actuator trench increase the yield of this assembly process.

Figure 15:
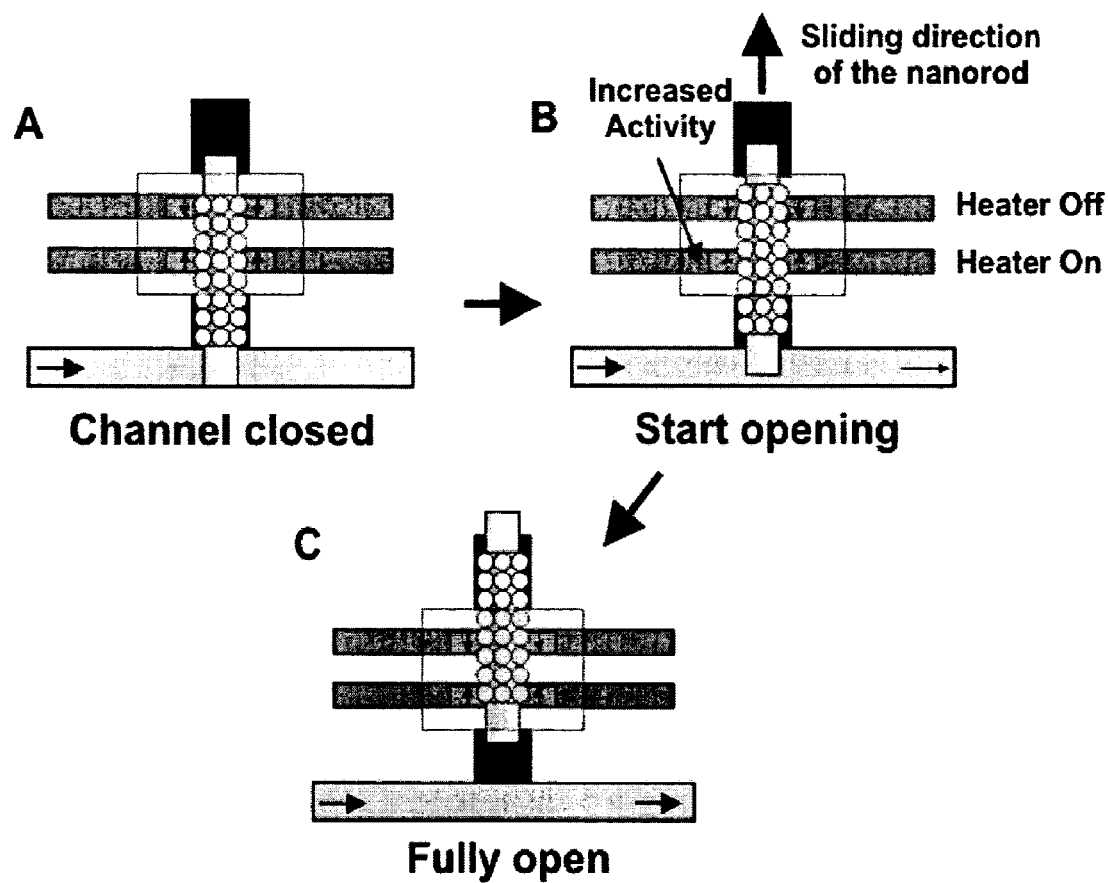
FIG. 15 provides a schematic diagram depicting operation of the valve.

The operation principals are demonstrated in FIG. 15. When one heater is on, the myosin-actin complexes on that heater have increased activities and slide the rod in the corresponding direction. In this way, the rod can open or close the microchannel.

The subject matter claimed is:

1. An actuator, comprising:
   a movable member that is coated at least in part with myosin;
   two separate arrays of actin filaments that are aligned with respect to a common axis but with opposite polarities, wherein both of the arrays are positioned to interact with the myosin that is coated on the movable member; and
   two separate energy-transmitting stripes that are associated with the arrays in a manner to selectively energize respective ones of the arrays, so that when one of the stripes is sufficiently energized, an actin/myosin interaction is such that the movable member is moved substantially linearly from its starting position in a direction parallel to the actin filaments within the arrays.

2. The actuator of claim 1, wherein the myosin comprises myosin S1 or heavy meromyosin.

3. The actuator of claim 1, wherein the movable member is a rod having a longitudinal dimension of about 100 nm to about 100 $\mu$m and a cross sectional dimension of about 20 nm to about 200 nm.

4. The actuator of claim 1, wherein the movable member is curved.

5. The actuator of claim 1, wherein the movable member comprises nickel, palladium, gold, platinum, cobalt, permalloy, chromium, or a combination thereof.

6. The actuator of claim 1, wherein the movable member comprises a polymeric material.

7. The actuator of claim 1 that is less than 100 $\mu$m in length in any of its 3 dimensional measurements.

8. The actuator of claim 1, wherein the actin/myosin interaction causes movement of the movable member along its longitudinal axis.

9. The actuator of claim 1, wherein the movement of the movable member is unidirectional.

10. The actuator of claim 8, wherein the movement of the movable member is bidirectional.

11. The actuator of claim 1, wherein at least one of the stripes transmits heat.

12. The actuator of claim 11, wherein the movable member is a rod, the arrays are arranged such that the actin filaments are parallel to the rod's longitudinal axis, and the rod is moved in a direction parallel to its longitudinal axis.

13. The actuator of claim 1, wherein the actin/myosin interaction is promoted by a source of chemical potential energy.

14. The actuator of claim 13, wherein the source of chemical potential energy is a nucleoside triphosphate.

15. The actuator of claim 13, wherein the source of chemical potential energy is adenosine triphosphate (ATP) or 2'-deoxy ATP.

16. The actuator of claim 1, wherein the stripes are associated with a source of energy, wherein energizing one of the stripes causes the movable member to move relative to its starting position.

17. A combination of at least two actuators of claim 1, wherein the actuators function in concert.

18. The actuator of claim 1, wherein when another one of the stripes is sufficiently energized, the actin/myosin interaction is such that the movable member is moved substantially linearly back towards its starting position.

* * * * *